US011389502B2

(12) United States Patent
Connaris et al.

(10) Patent No.: US 11,389,502 B2
(45) Date of Patent: Jul. 19, 2022

(54) CELL MODULATION

(71) Applicant: OMIDEON LIMITED, Fife (GB)

(72) Inventors: Helen Connaris, St. Andrews (GB); Judith Telford, St. Andrews (GB); Graeme Rogers, St. Andrews (GB)

(73) Assignee: OMIDEON LIMITED, Fife (GB)

( * ) Notice: Subject to any disclaimer, the term of this patent is extended or adjusted under 35 U.S.C. 154(b) by 184 days.

(21) Appl. No.: 16/332,926

(22) PCT Filed: Sep. 20, 2017

(86) PCT No.: PCT/GB2017/052808
§ 371 (c)(1),
(2) Date: Mar. 13, 2019

(87) PCT Pub. No.: WO2018/055373
PCT Pub. Date: Mar. 29, 2018

(65) Prior Publication Data
US 2019/0247460 A1    Aug. 15, 2019

(30) Foreign Application Priority Data
Sep. 20, 2016  (GB) ..................... 1616006

(51) Int. Cl.
*A61K 38/16*   (2006.01)
*A61K 38/17*   (2006.01)
*A61P 35/00*   (2006.01)

(52) U.S. Cl.
CPC .......... *A61K 38/164* (2013.01); *A61K 38/178* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2002/0025320 A1 | 2/2002 | Boyaka et al. | |
| 2004/0072256 A1 | 4/2004 | Mandelboim et al. | |
| 2005/0084903 A1 | 4/2005 | Kim et al. | |

FOREIGN PATENT DOCUMENTS

| | | | |
|---|---|---|---|
| EP | 2799086 | 11/2014 | |
| WO | 00/10388 | 3/2000 | |
| WO | 2002/094869 | 11/2002 | |
| WO | 2007/075921 | 7/2007 | |
| WO | 2008/053486 | 5/2008 | |
| WO | WO-2009049234 A2 * | 4/2009 | ............. A61K 31/40 |
| WO | 2010/005737 | 1/2010 | |
| WO | 2010/029312 | 3/2010 | |
| WO | 2010/052492 | 5/2010 | |
| WO | 2010/102112 | 9/2010 | |
| WO | 2014/052621 | 4/2014 | |
| WO | 2015/110831 | 7/2015 | |
| WO | WO-2018006034 A1 * | 1/2018 | ............. C07K 16/32 |
| WO | 2018/055365 | 3/2018 | |
| WO | 2018/055370 | 3/2018 | |

OTHER PUBLICATIONS

UniprotKB-P0C6E9 Mar. 18, 2008.*
Chatterjee et al. Cancer Immunol Immunother. 1994 38:75-82.*
Corcos et al. Cancer Medicine 2013; 2(4):421-426.*
Ferreira, Daniela & Adega, Filomena & Chaves, Raquel. (2013). The Importance of Cancer Cell Lines as in vitro Models in Cancer Methylome Analysis and Anticancer Drugs Testing. 10.5772/1745.*
Chakraborty et al. ecancer 2012, 6:ed16 DOI:10.3332/ecancer.2012.ed16.*
Boraston et al Biochemistry 2007, 46, 11352-11360.*
Baradaran et al. "Newcastle Disease Virus Hemagglutinin Neuraminidase as a Potential Cancer Targeting Agent", Journal of Cancer, 7,(4):462-466 (2016).
Chen at al, "Preserving Sialic Acid-dependent Pattern Recognition by CD24-Siglec G Interaction for Therapy of Polybacterial Sepsis" Nature Biotechnology, 29(5):428-435 (2011).
Connaris et al. "Enhancing the Receptor Affinity of the Sialic Acid-binding Domain of Vibrio cholerae Sialidase through Multivalency" Journal of Biological Chemistry, 284(11):7339-7351 (2009).
Connaris et al. "Prevention of influenza, by targeting host receptors using engineered proteins" Proceedings of the National Academy of Sciences, 111(17):6401-6406 (2014).
Gasiorowski et al. "The impact of neuraminidase on apoptosis in cultures of blood lymphocytes isolated from rats bearing morris hepatoma" Cellular & molecular biology letters, pp. 389-399, URL: http://www.cmbl.org.pl/pdf/Vol9_p389.pdf (2004).
Govorkova et al. "Sialic Acid-Binding Protein Sp2CBMTD Protects Mice against Lethal Challenge with Emerging Influenza A (H7N9) Virus" Antimicrobial Agents and Chemothe, American Society for Microbiology, 59(3):1495-1504 (2015).
Grata-Borkowska et al. "Effects of neuraminidase on apoptosis of blood lymphocytes in rats with implanted Morris tumor" Journal of physiology and pharmacology: an official journal of the Polish Physiological Society, p. 253, URL: http://www.jpp.krakow.pl/journal/archive/11_07_s5/pdf/253_11_07_s5_article.pdf (2007).
International Preliminary Report on Patentability corresponding to International Patent Application No. PCT/GB2017/052800, dated Mar. 26, 2019, 6 pages.
International Preliminary Report on Patentability corresponding to International Patent Application No. PCT/GB2017/052805, dated Mar. 26, 2019, 8 pages.
International Preliminary Report on Patentability corresponding to International Patent Application No. PCT/GB2017/052808, dated Mar. 26, 2019, 9 pages.
Manco et al. "Pneumococcal Neuraminidases A and B Both Have Essential Roles during Infection of the Respiratory Tract and Sepsis" Infection and Immunity, 74(7):4014-4020 (2006).
Simmons et al, "Immunospecific Regression of Methylcholanthrene Fibrosarcoma With the Use of Neuraminidase, II, Intratumor Injections of Neuraminidase" SUR, 71(4):556-564 (1972).

(Continued)

*Primary Examiner* — Oluwatosin A Ogunbiyi
(74) *Attorney, Agent, or Firm* — Myers Bigel, P.A.

(57) ABSTRACT

The present disclosure provides molecules which modulate cell growth. These molecules include those that bind sialic acid which may find application in the treatment and/or prevention of cell proliferation and/or differentiation disorders, cancer and/or it's migration and/or spread.

9 Claims, 23 Drawing Sheets

Specification includes a Sequence Listing.

(56) References Cited

OTHER PUBLICATIONS

Simmons et al. "Regression of Established Methylcholanthrene Tumors By Intratumor Injections of Vibrio Cholerae Neuraminidase" Journal of Surgical Onco, 4(4):298-305 (1972) Abstract.

Written Opinion and International Search Report corresponding to International Patent Application No. PCT/GB2017/052800, dated Mar. 29, 2018, 10 pages.

Written Opinion and International Search Report corresponding to International Patent Application No. PCT/GB2017/052805, dated Mar. 29, 2018, 11 pages.

Written Opinion and International Search Report corresponding to International Patent Application No. PCT/GB2017/052808, dated Mar. 29, 2018, 16 pages.

Yang et al. "Structural characterization of the carbohydrate-binding module of NanA sialdase, a pneumococcal virulence factor" BMC Structural Biology, 15(1):15(2015).

Alias "Multivalent sialic acid binding proteins as novel therapeutics for influenza and parainfluenza infection" PhD Thesis at University of St Andrews, 252 pages (2013).

Knop "Stimulatory effect of Vibrio cholera neuraminidase on the antibody response to various antigens" Immunology, 34:181-187 (1978).

Research Councils UK, Gateway to Research "Exploiting a sialic acid binding domain" University of St Andrews, 4 pages, accessed Jun. 1, 2017 from http://gtr.rcuk.ac.uk/projects?ref=BB%FE001912%2F1.

Rios et al. "Experimental Cancer Immunotherapy: modification of tumor cells to increase immunogenicity" Annals New York Academy of Sciences, 276:45-60 (1976).

Simmons et al. "Immunospecific Regression of Methylcholanthrene Fibrosarcoma With the Use of Neuraminidase: III. Synergistic Effect of BCG and Neuraminidase Treated Tumor Cells" Ann. Surg., 176 (2):188-194 (1972).

Crost et al. "The mucin-degradation strategy of Ruminococcus gnavus: The importance of intramolecular transsialidases" Gut Microbes, 7(4):302-312 2016.

Lipničanová et al. "Diversity of sialidases found in the human body—A review" Intl. J. Biol. Macromolecules, 148:857-868 2020.

Büll, Christian, et al., "Sialic Acids Sweeten a Tumor's Life", Cancer Research 74(12), 2014, 3199-3204.

Dobie, Christopher, et al., "Insights into the roll of sialylation in cancer progression and metastasis", British Cancer Journal 124, 2021, 76-90.

Pearce, Oliver M T, et al., "Sialic Acids in Cancer Biology and Immunity", Glycobiology 26(2), 2016, 111-128.

\* cited by examiner

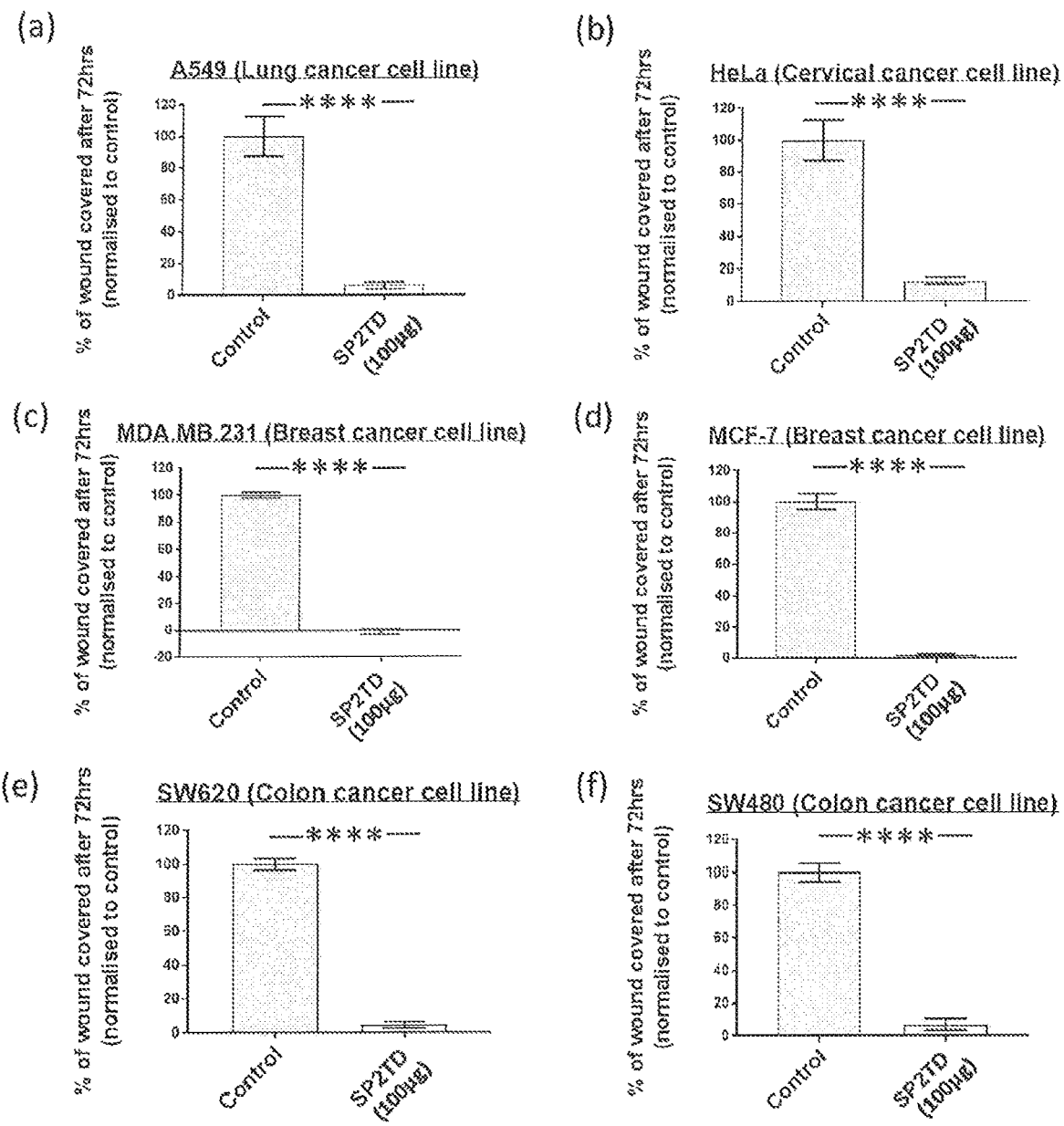
Figures 7A-F

Figure 11B:
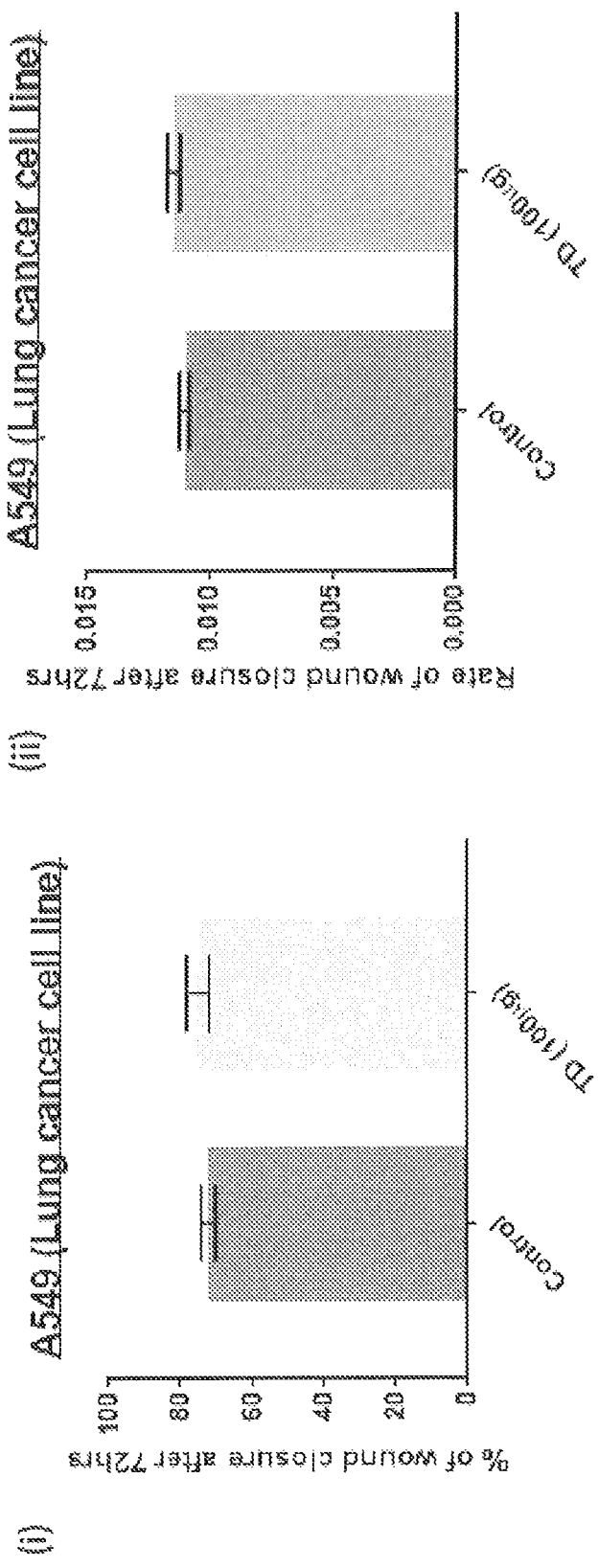

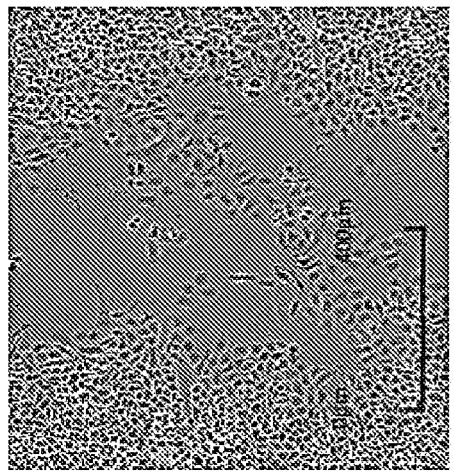
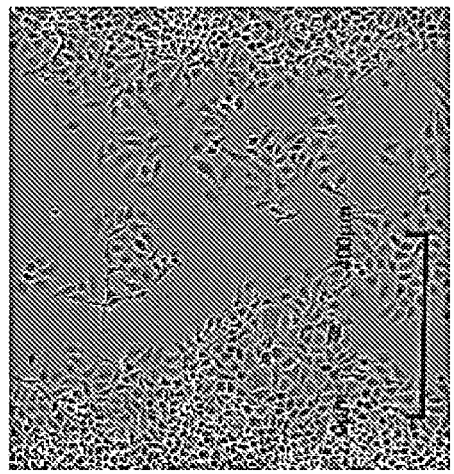
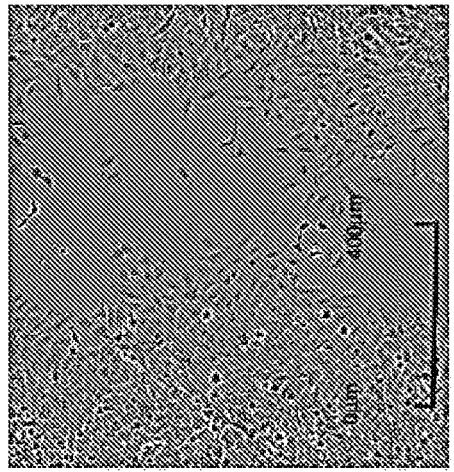
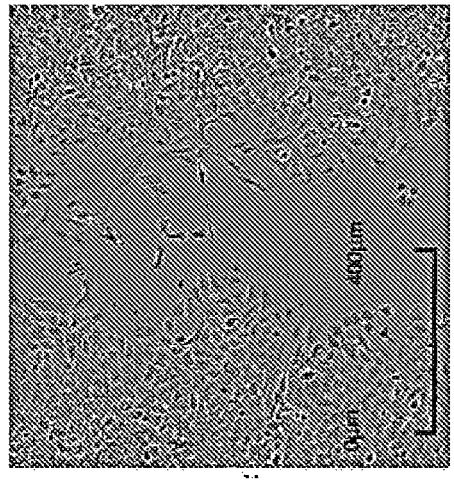
Figure 11A

A.
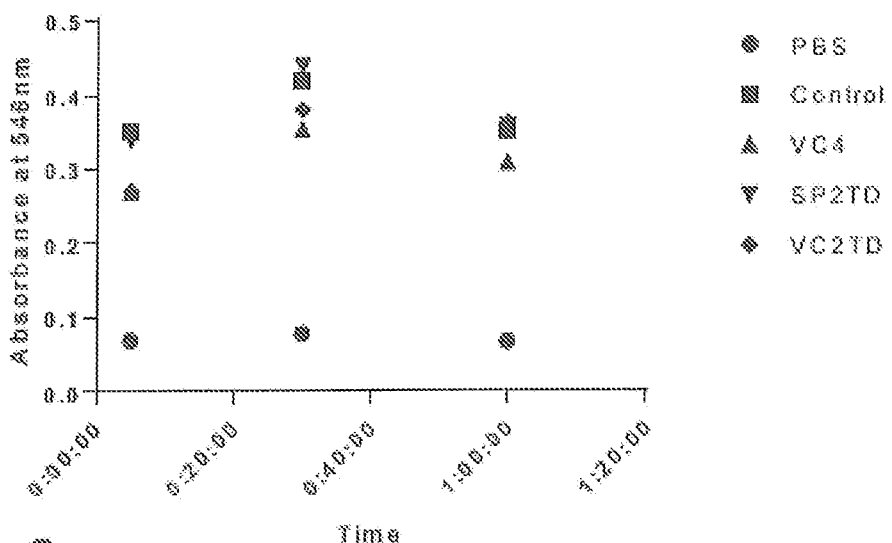
C.
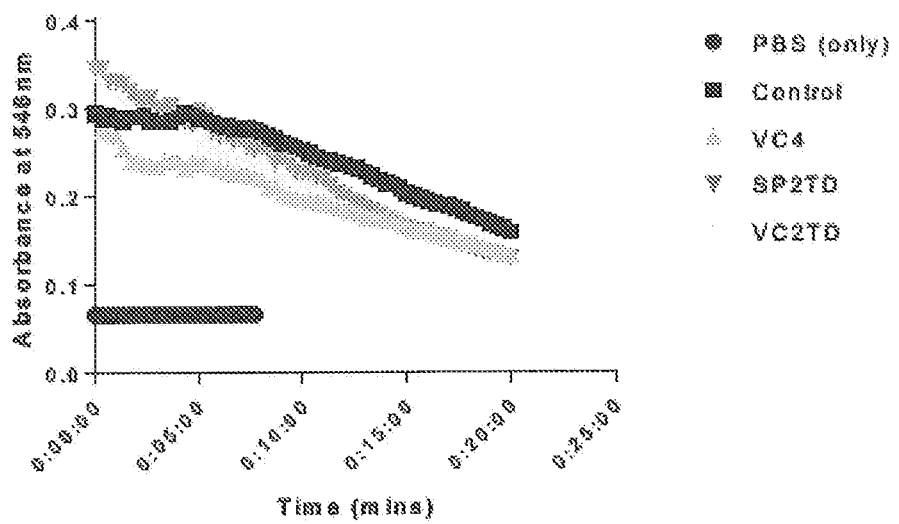
Figures 14A & C

B.
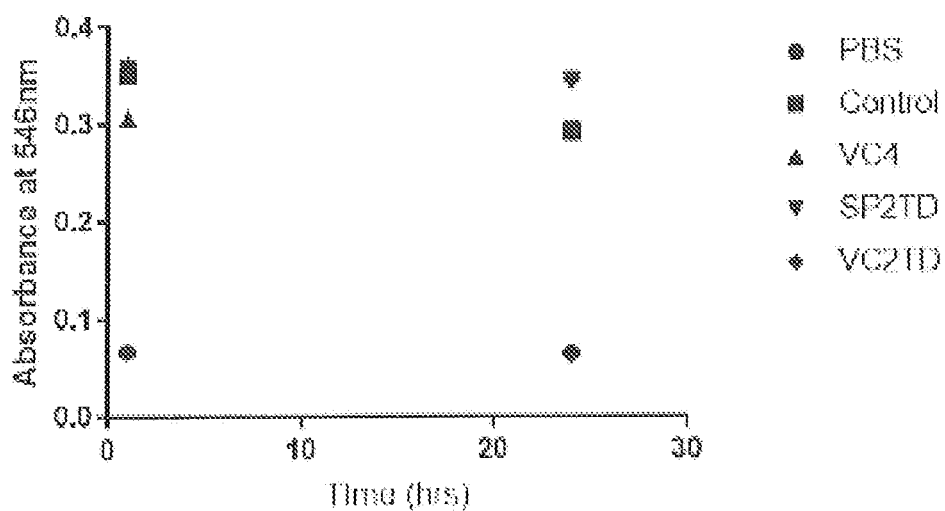
D.
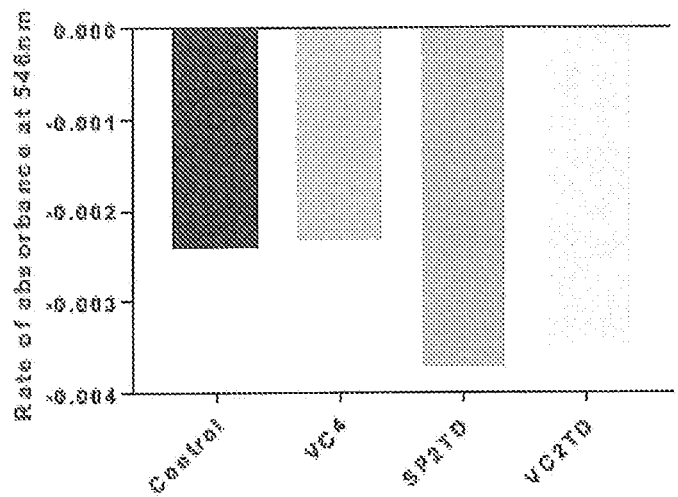
Figure 14 B & D

SEQUENCE LISTING

<160> NUMBER OF SEQ ID NOS: 12

<210> SEQ ID NO 1
<211> LENGTH: 781
<212> TYPE: PRT
<213> ORGANISM: Vibrio cholerae

<400> SEQUENCE: 1

Met Arg Phe Lys Asn Val Lys Lys Thr Ala Leu Met Leu Ala Met Phe
1 5 10 15

Gly Met Ala Thr Ser Ser Asn Ala Ala Leu Phe Asp Tyr Asn Ala Thr
20 25 30

Gly Asp Thr Glu Phe Asp Ser Pro Ala Lys Gln Gly Trp Met Gln Asp
35 40 45

Asn Thr Asn Asn Gly Ser Gly Val Leu Thr Asn Ala Asp Gly Met Pro
50 55 60

Ala Trp Leu Val Gln Gly Ile Gly Gly Arg Ala Gln Trp Thr Tyr Ser
65 70 75 80

Leu Ser Thr Asn Gln His Ala Gln Ala Ser Ser Phe Gly Trp Arg Met
85 90 95

Thr Thr Glu Met Lys Val Leu Ser Gly Gly Met Ile Thr Asn Tyr Tyr
100 105 110

Ala Asn Gly Thr Gln Arg Val Leu Pro Ile Ile Ser Leu Asp Ser Ser
115 120 125

Gly Asn Leu Val Val Glu Phe Glu Gly Gln Thr Gly Arg Thr Val Leu
130 135 140

Ala Thr Gly Thr Ala Ala Thr Glu Tyr His Lys Phe Glu Leu Val Phe
145 150 155 160

Leu Pro Gly Ser Asn Pro Ser Ala Ser Phe Tyr Phe Asp Gly Lys Leu
165 170 175

Ile Arg Asp Asn Ile Gln Pro Thr Ala Ser Lys Gln Asn Met Ile Val
180 185 190

Trp Gly Asn Gly Ser Ser Asn Thr Asp Gly Val Ala Ala Tyr Arg Asp
195 200 205

Ile Lys Phe Glu Ile Gln Gly Asp Val Ile Phe Arg Gly Pro Asp Arg
210 215 220

Ile Pro Ser Ile Val Ala Ser Ser Val Thr Pro Gly Val Val Thr Ala
225 230 235 240

Phe Ala Glu Lys Arg Val Gly Gly Gly Asp Pro Gly Ala Leu Ser Asn
245 250 255

Thr Asn Asp Ile Ile Thr Arg Thr Ser Arg Asp Gly Gly Ile Thr Trp
260 265 270

Asp Thr Glu Leu Asn Leu Thr Glu Gln Ile Asn Val Ser Asp Glu Phe
275 280 285

Asp Phe Ser Asp Pro Arg Pro Ile Tyr Asp Pro Ser Ser Asn Thr Val
290 295 300

Leu Val Ser Tyr Ala Arg Trp Pro Thr Asp Ala Ala Gln Asn Gly Asp
305 310 315 320

```
Arg Ile Lys Pro Trp Met Pro Asn Gly Ile Phe Tyr Ser Val Tyr Asp
            325                 330                 335

Val Ala Ser Gly Asn Trp Gln Ala Pro Ile Asp Val Thr Asp Gln Val
            340                 345                 350

Lys Glu Arg Ser Phe Gln Ile Ala Gly Trp Gly Ser Glu Leu Tyr
            355                 360             365

Arg Arg Asn Thr Ser Leu Asn Ser Gln Gln Asp Trp Gln Ser Asn Ala
    370                 375                 380

Lys Ile Arg Ile Val Asp Gly Ala Ala Asn Gln Ile Gln Val Ala Asp
385                 390                 395                 400

Gly Ser Arg Lys Tyr Val Val Thr Leu Ser Ile Asp Glu Ser Gly Gly
                405                 410                 415

Leu Val Ala Asn Leu Asn Gly Val Ser Ala Pro Ile Ile Leu Gln Ser
                420                 425                 430

Glu His Ala Lys Val His Ser Phe His Asp Tyr Glu Leu Gln Tyr Ser
            435                 440                 445

Ala Leu Asn His Thr Thr Thr Leu Phe Val Asp Gly Gln Gln Ile Thr
    450                 455                 460

Thr Trp Ala Gly Glu Val Ser Gln Glu Asn Asn Ile Gln Phe Gly Asn
465                 470                 475                 480

Ala Asp Ala Gln Ile Asp Gly Arg Leu His Val Gln Lys Ile Val Leu
                485                 490                 495

Thr Gln Gln Gly His Asn Leu Val Glu Phe Asp Ala Phe Tyr Leu Ala
                500                 505                 510

Gln Gln Thr Pro Glu Val Glu Lys Asp Leu Glu Lys Leu Gly Trp Thr
            515                 520                 525

Lys Ile Lys Thr Gly Asn Thr Met Ser Leu Tyr Gly Asn Ala Ser Val
530                 535                 540

Asn Pro Gly Pro Gly His Gly Ile Thr Leu Thr Arg Gln Gln Asn Ile
545                 550                 555                 560

Ser Gly Ser Gln Asn Gly Arg Leu Ile Tyr Pro Ala Ile Val Leu Asp
                565                 570                 575

Arg Phe Phe Leu Asn Val Met Ser Ile Tyr Ser Asp Asp Gly Gly Ser
            580                 585                 590

Asn Trp Gln Thr Gly Ser Thr Leu Pro Ile Pro Phe Arg Trp Lys Ser
            595                 600                 605

Ser Ser Ile Leu Glu Thr Leu Glu Pro Ser Glu Ala Asp Met Val Glu
    610                 615                 620

Leu Gln Asn Gly Asp Leu Leu Thr Ala Arg Leu Asp Phe Asn Gln
625                 630                 635                 640

Ile Val Asn Gly Val Asn Tyr Ser Pro Arg Gln Gln Phe Leu Ser Lys
                645                 650                 655

Asp Gly Gly Ile Thr Trp Ser Leu Leu Glu Ala Asn Asn Ala Asn Val
                660                 665                 670

Phe Ser Asn Ile Ser Thr Gly Thr Val Asp Ala Ser Ile Thr Arg Phe
    675                 680                 685

Glu Gln Ser Asp Gly Ser His Phe Leu Leu Phe Thr Asn Pro Gln Gly
    690                 695                 700

Asn Pro Ala Gly Thr Asn Gly Arg Gln Asn Leu Gly Leu Trp Phe Ser
705                 710                 715                 720

Phe Asp Glu Gly Val Thr Trp Lys Gly Pro Ile Gln Leu Val Asn Gly
                725                 730                 735
```

```
Ala Ser Ala Tyr Ser Asp Ile Tyr Gln Leu Asp Ser Glu Asn Ala Ile
            740                 745                 750

Val Ile Val Glu Thr Asp Asn Ser Asn Met Arg Ile Leu Arg Met Pro
        755                 760                 765

Ile Thr Leu Leu Lys Gln Lys Leu Thr Leu Ser Gln Asn
    770                 775                 780

<210> SEQ ID NO 2
<211> LENGTH: 192
<212> TYPE: PRT
<213> ORGANISM: Vibrio cholerae

<400> SEQUENCE: 2

Ala Leu Phe Asp Tyr Asn Ala Thr Gly Asp Thr Glu Phe Asp Ser Pro
1               5                   10                  15

Ala Lys Gln Gly Trp Met Gln Asp Asn Thr Asn Asn Gly Ser Gly Val
            20                  25                  30

Leu Thr Asn Ala Asp Gly Met Pro Ala Trp Leu Val Gln Gly Ile Gly
        35                  40                  45

Gly Arg Ala Gln Trp Thr Tyr Ser Leu Ser Thr Asn Gln His Ala Gln
    50                  55                  60

Ala Ser Ser Phe Gly Trp Arg Met Thr Thr Glu Met Lys Val Leu Ser
65                  70                  75                  80

Gly Gly Met Ile Thr Asn Tyr Tyr Ala Asn Gly Thr Gln Arg Val Leu
                85                  90                  95

Pro Ile Ile Ser Leu Asp Ser Ser Gly Asn Leu Val Val Glu Phe Glu
            100                 105                 110

Gly Gln Thr Gly Arg Thr Val Leu Ala Thr Gly Thr Ala Ala Thr Glu
        115                 120                 125

Tyr His Lys Phe Glu Leu Val Phe Leu Pro Gly Ser Asn Pro Ser Ala
    130                 135                 140

Ser Phe Tyr Phe Asp Gly Lys Leu Ile Arg Asp Asn Ile Gln Pro Thr
145                 150                 155                 160

Ala Ser Lys Gln Asn Met Ile Val Trp Gly Asn Gly Ser Ser Asn Thr
                165                 170                 175

Asp Gly Val Ala Ala Tyr Arg Asp Ile Lys Phe Glu Ile Gln Gly Asp
            180                 185                 190

<210> SEQ ID NO 3
<211> LENGTH: 1035
<212> TYPE: PRT
<213> ORGANISM: Streptococcus pneumoniae

<400> SEQUENCE: 3

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
            20                  25                  30

Ser Val Gly Ala Val Ser Met Ile Val Gly Ala Val Val Phe Gly Thr
        35                  40                  45

Ser Pro Val Leu Ala Gln Glu Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95
```

```
Glu Arg Lys Asp Lys Gln Glu Glu Lys Ile Pro Arg Asp Tyr Tyr Ala
                100                 105                 110
Arg Asp Leu Glu Asn Val Glu Thr Val Ile Glu Lys Glu Asp Val Glu
            115                 120                 125
Thr Asn Ala Ser Asn Gly Gln Arg Val Asp Leu Ser Ser Glu Leu Asp
        130                 135                 140
Lys Leu Lys Lys Leu Glu Asn Ala Thr Val His Met Glu Phe Lys Pro
145                 150                 155                 160
Asp Ala Lys Ala Pro Ala Phe Tyr Asn Leu Phe Ser Val Ser Ser Ala
                165                 170                 175
Thr Lys Lys Asp Glu Tyr Phe Thr Met Ala Val Tyr Asn Asn Thr Ala
            180                 185                 190
Thr Leu Glu Gly Arg Gly Ser Asp Gly Lys Gln Phe Tyr Asn Asn Tyr
        195                 200                 205
Asn Asp Ala Pro Leu Lys Val Lys Pro Gly Gln Trp Asn Ser Val Thr
    210                 215                 220
Phe Thr Val Glu Lys Pro Thr Ala Glu Leu Pro Lys Gly Arg Val Arg
225                 230                 235                 240
Leu Tyr Val Asn Gly Val Leu Ser Arg Thr Ser Leu Arg Ser Gly Asn
                245                 250                 255
Phe Ile Lys Asp Met Pro Asp Val Thr His Val Gln Ile Gly Ala Thr
            260                 265                 270
Lys Arg Ala Asn Asn Thr Val Trp Gly Ser Asn Leu Gln Ile Arg Asn
        275                 280                 285
Leu Thr Val Tyr Asn Arg Ala Leu Thr Pro Glu Glu Val Gln Lys Arg
    290                 295                 300
Ser Gln Leu Phe Lys Arg Ser Asp Leu Glu Lys Lys Leu Pro Glu Gly
305                 310                 315                 320
Ala Ala Leu Thr Glu Lys Thr Asp Ile Phe Glu Ser Gly Arg Asn Gly
                325                 330                 335
Lys Pro Asn Lys Asp Gly Ile Lys Ser Tyr Arg Ile Pro Ala Leu Leu
            340                 345                 350
Lys Thr Asp Lys Gly Thr Leu Ile Ala Gly Ala Asp Glu Arg Arg Leu
        355                 360                 365
His Ser Ser Asp Trp Gly Asp Ile Gly Met Val Ile Arg Arg Ser Glu
    370                 375                 380
Asp Asn Gly Lys Thr Trp Gly Asp Arg Val Thr Ile Thr Asn Leu Arg
385                 390                 395                 400
Asp Asn Pro Lys Ala Ser Asp Pro Ser Ile Gly Ser Pro Val Asn Ile
                405                 410                 415
Asp Met Val Leu Val Gln Asp Pro Glu Thr Lys Arg Ile Phe Ser Ile
            420                 425                 430
Tyr Asp Met Phe Pro Glu Gly Lys Gly Ile Phe Gly Met Ser Ser Gln
        435                 440                 445
Lys Glu Glu Ala Tyr Lys Lys Ile Asp Gly Lys Thr Tyr Gln Ile Leu
    450                 455                 460
Tyr Arg Glu Gly Glu Lys Gly Ala Tyr Thr Ile Arg Glu Asn Gly Thr
465                 470                 475                 480
Val Tyr Thr Pro Asp Gly Lys Ala Thr Asp Tyr Arg Val Val Val Asp
                485                 490                 495
Pro Val Lys Pro Ala Tyr Ser Asp Lys Gly Asp Leu Tyr Lys Gly Asn
            500                 505                 510
Gln Leu Leu Gly Asn Ile Tyr Phe Thr Thr Asn Lys Thr Ser Pro Phe
```

-continued

```
            515                 520                 525
Arg Ile Ala Lys Asp Ser Tyr Leu Trp Met Ser Tyr Ser Asp Asp
        530                 535                 540
Gly Lys Thr Trp Ser Ala Pro Gln Asp Ile Thr Pro Met Val Lys Ala
545                 550                 555                 560
Asp Trp Met Lys Phe Leu Gly Val Gly Pro Gly Thr Gly Ile Val Leu
                565                 570                 575
Arg Asn Gly Pro His Lys Gly Arg Ile Leu Ile Pro Val Tyr Thr Thr
                580                 585                 590
Asn Asn Val Ser His Leu Asn Gly Ser Gln Ser Ser Arg Ile Ile Tyr
                595                 600                 605
Ser Asp Asp His Gly Lys Thr Trp His Ala Gly Glu Ala Val Asn Asp
        610                 615                 620
Asn Arg Gln Val Asp Gly Gln Lys Ile His Ser Ser Thr Met Asn Asn
625                 630                 635                 640
Arg Arg Ala Gln Asn Thr Glu Ser Thr Val Val Gln Leu Asn Asn Gly
                645                 650                 655
Asp Val Lys Leu Phe Met Arg Gly Leu Thr Gly Asp Leu Gln Val Ala
                660                 665                 670
Thr Ser Lys Asp Gly Gly Val Thr Trp Glu Lys Asp Ile Lys Arg Tyr
        675                 680                 685
Pro Gln Val Lys Asp Val Tyr Val Gln Met Ser Ala Ile His Thr Met
690                 695                 700
His Glu Gly Lys Glu Tyr Ile Ile Leu Ser Asn Ala Gly Gly Pro Lys
705                 710                 715                 720
Arg Glu Asn Gly Met Val His Leu Ala Arg Val Glu Glu Asn Gly Glu
                725                 730                 735
Leu Thr Trp Leu Lys His Asn Pro Ile Gln Lys Gly Glu Phe Ala Tyr
                740                 745                 750
Asn Ser Leu Gln Glu Leu Gly Asn Gly Glu Tyr Gly Ile Leu Tyr Glu
        755                 760                 765
His Thr Glu Lys Gly Gln Asn Ala Tyr Thr Leu Ser Phe Arg Lys Phe
        770                 775                 780
Asn Trp Asp Phe Leu Ser Lys Asp Leu Ile Ser Pro Thr Glu Ala Lys
785                 790                 795                 800
Val Lys Arg Thr Arg Glu Met Gly Lys Gly Val Ile Gly Leu Glu Phe
                805                 810                 815
Asp Ser Glu Val Leu Val Asn Lys Ala Pro Thr Leu Gln Leu Ala Asn
                820                 825                 830
Gly Lys Thr Ala Arg Phe Met Thr Gln Tyr Asp Thr Lys Thr Leu Leu
        835                 840                 845
Phe Thr Val Asp Ser Glu Asp Met Gly Gln Lys Val Thr Gly Leu Ala
        850                 855                 860
Glu Gly Ala Ile Glu Ser Met His Asn Leu Pro Val Ser Val Ala Gly
865                 870                 875                 880
Thr Lys Leu Ser Asn Gly Met Asn Gly Ser Glu Ala Ala Val His Glu
                885                 890                 895
Val Pro Glu Tyr Thr Gly Pro Leu Gly Thr Ser Gly Glu Glu Pro Ala
                900                 905                 910
Pro Thr Val Glu Lys Pro Glu Tyr Thr Gly Leu Gly Thr Ser Gly
        915                 920                 925
Glu Glu Pro Ala Pro Thr Val Glu Lys Pro Glu Tyr Thr Gly Pro Leu
930                 935                 940
```

```
Gly Thr Ala Gly Glu Glu Ala Ala Pro Thr Val Glu Lys Pro Glu Phe
945                 950                 955                 960

Thr Gly Gly Val Asn Gly Thr Glu Pro Ala Val His Glu Ile Ala Glu
                965                 970                 975

Tyr Lys Gly Ser Asp Ser Leu Val Thr Leu Thr Thr Glu Asp Tyr
            980                 985                 990

Thr Tyr Lys Ala Pro Leu Ala Gln Gln Ala Leu Pro Glu Thr Gly Asn
        995                 1000                1005

Lys Glu Ser Asp Leu Leu Ala Ser Leu Gly Leu Thr Ala Phe Phe
    1010                1015                1020

Leu Gly Leu Phe Thr Leu Gly Lys Lys Arg Glu Gln
    1025                1030                1035

<210> SEQ ID NO 4
<211> LENGTH: 185
<212> TYPE: PRT
<213> ORGANISM: Streptococcus pneumoniae

<400> SEQUENCE: 4

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
            20                  25                  30

Thr Val His Met Glu Phe Lys Pro Asp Ala Lys Ala Pro Ala Phe Tyr
        35                  40                  45

Asn Leu Phe Ser Val Ser Ser Ala Thr Lys Lys Asp Glu Tyr Phe Thr
50                  55                  60

Met Ala Val Tyr Asn Asn Thr Ala Thr Leu Glu Gly Arg Gly Ser Asp
65                  70                  75                  80

Gly Lys Gln Phe Tyr Asn Asn Tyr Asn Asp Ala Pro Leu Lys Val Lys
                85                  90                  95

Pro Gly Gln Trp Asn Ser Val Thr Phe Thr Val Glu Lys Pro Thr Ala
            100                 105                 110

Glu Leu Pro Lys Gly Arg Val Arg Leu Tyr Val Asn Gly Val Leu Ser
        115                 120                 125

Arg Thr Ser Leu Arg Ser Gly Asn Phe Ile Lys Asp Met Pro Asp Val
    130                 135                 140

Thr His Val Gln Ile Gly Ala Thr Lys Arg Ala Asn Asn Thr Val Trp
145                 150                 155                 160

Gly Ser Asn Leu Gln Ile Arg Asn Leu Thr Val Tyr Asn Arg Ala Leu
                165                 170                 175

Thr Pro Glu Glu Val Gln Lys Arg Ser
            180                 185

<210> SEQ ID NO 5
<211> LENGTH: 438
<212> TYPE: PRT
<213> ORGANISM: Pseudomonas aeruginosa

<400> SEQUENCE: 5

Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
            20                  25                  30

Gly Ser Leu Tyr Leu Ile Tyr Arg Arg Ala Thr Glu His Val Gly Gly
        35                  40                  45
```

-continued

```
Ser Asp Gly Arg Val Val Phe Ser Lys Leu Glu Gly Ile Trp Ser
 50                  55                  60

Ala Pro Thr Ile Val Ala Gln Ala Gly Gly Gln Asp Phe Arg Asp Val
 65                  70                  75                  80

Ala Gly Gly Thr Met Pro Ser Gly Arg Ile Val Ala Ala Ser Thr Val
                 85                  90                  95

Tyr Glu Thr Gly Glu Val Lys Val Tyr Val Ser Asp Asp Ser Gly Val
                100                 105                 110

Thr Trp Val His Lys Phe Thr Leu Ala Arg Gly Gly Ala Asp Tyr Asn
                115                 120                 125

Phe Ala His Gly Lys Ser Phe Gln Val Gly Ala Arg Tyr Val Ile Pro
                130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Gly Ser Thr Ile Tyr Ser Gly
                165                 170                 175

Asn Thr Pro Tyr Asn Glu Thr Ser Tyr Leu Pro Val Gly Asp Gly Val
                180                 185                 190

Ile Leu Ala Val Ala Arg Val Gly Ser Gly Ala Gly Gly Ala Leu Arg
                195                 200                 205

Gln Phe Ile Ser Leu Asp Asp Gly Gly Thr Trp Thr Asp Gln Gly Asn
210                 215                 220

Val Thr Ala Gln Asn Gly Asp Ser Thr Asp Ile Leu Val Ala Pro Ser
225                 230                 235                 240

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
                260                 265                 270

Ala Lys Ala Val Ala Gly Ser Ser Gly Trp Thr Glu Arg Val Pro Val
                275                 280                 285

Tyr Ser Ala Pro Ala Ala Ser Gly Tyr Thr Ser Gln Val Val Leu Gly
290                 295                 300

Gly Arg Arg Ile Leu Gly Asn Leu Phe Arg Glu Thr Ser Ser Thr Thr
305                 310                 315                 320

Ser Gly Ala Tyr Gln Phe Glu Val Tyr Leu Gly Gly Val Pro Asp Phe
                325                 330                 335

Glu Ser Asp Trp Phe Ser Val Ser Ser Asn Ser Leu Tyr Thr Leu Ser
                340                 345                 350

His Gly Leu Gln Arg Ser Pro Arg Arg Val Val Glu Phe Ala Arg
                355                 360                 365

Ser Ser Ser Pro Ser Thr Trp Asn Ile Val Met Pro Ser Tyr Phe Asn
370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
                405                 410                 415

Gly Gly Ile Asp Asn Ser Ala Thr Thr Arg Phe Ala Thr Gly Tyr Tyr
                420                 425                 430

Arg Val Arg Ala Trp Ile
                435
```

<210> SEQ ID NO 6
<211> LENGTH: 106

```
<212> TYPE: PRT
<213> ORGANISM: Pseudomonas aeruginosa

<400> SEQUENCE: 6

Val Pro Asp Phe Glu Ser Asp Trp Phe Ser Val Ser Asn Ser Leu
1               5                   10                  15

Tyr Thr Leu Ser His Gly Leu Gln Arg Ser Pro Arg Val Val
                20                  25                  30

Glu Phe Ala Arg Ser Ser Pro Ser Thr Trp Asn Ile Val Met Pro
                35                  40                  45

Ser Tyr Phe Asn Asp Gly Gly His Lys Gly Ser Gly Ala Gln Val Glu
    50                  55                  60

Val Gly Ser Leu Asn Ile Arg Leu Gly Thr Gly Ala Ala Val Trp Gly
65                  70                  75                  80

Thr Gly Tyr Phe Gly Gly Ile Asp Asn Ser Ala Thr Thr Arg Phe Ala
                85                  90                  95

Thr Gly Tyr Tyr Arg Val Arg Ala Trp Ile
                100                 105

<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

Ala Leu Asn Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Linker

<400> SEQUENCE: 8

Leu Gln Ala Leu Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Linker

<400> SEQUENCE: 9

Gly Gly Asn Ser Gly
1               5

<210> SEQ ID NO 10
<211> LENGTH: 10
<212> TYPE: PRT
<213> ORGANISM: Artificial Sequence
<220> FEATURE:
<223> OTHER INFORMATION: Linker

<400> SEQUENCE: 10

Ala Leu Asn Gly Ser Gly Gly Ser Gly
1               5                   10
```

```
<210> SEQ ID NO 11
<211> LENGTH: 10
<212> TYPE: PRT
<213> ORGANISM: Artificial Sequence
<220> FEATURE:
<223> OTHER INFORMATION: Linker

<400> SEQUENCE: 11

Leu Gln Ala Leu Gly Gly Gly Gly Ser Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Linker

<400> SEQUENCE: 12

Ala Leu Asn Gly Ser Gly Gly Gly Ser Gly Gly Gly Gly Ser Gly
1               5                   10                  15
```

CELL MODULATION

STATEMENT OF PRIORITY

This application is a 35 U.S.C. § 371 national phase application of International Application Serial No. PCT/GB2017/052808, filed Sep. 20, 2017, which claims the benefit, of United Kingdom Patent Application No. 1616006.1, filed Sep. 20, 2016, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 1476.6 Replacement Seq List ST25.txt, 25,202 bytes in size, generated on Mar. 9, 2022, and filed via EFS-Web, is provided in lieu of a paper copy. This Sequence Listing is hereby incorporated herein by reference into the specification for its disclosures.

FIELD OF THE INVENTION

The present invention provides molecules for use in modulating cell growth and/or activity and for use in methods of treating or preventing cancer, its migration and/or spread.

BACKGROUND TO THE INVENTION

It is well known that some lectins, which are glycoproteins of non-immune origin, exhibit an ability to induce apoptosis in malignant cells and thus demonstrate anti-cancer properties. This phenomenon occurs, in part, through the interaction of these lectins with specific glycan receptors on immune cells (Yau et al., 2015).

One such lectin is Viscumin from mistletoe, which is a toxin that binds to cellular receptors that are glycosylated with α2,6 sialyllactose (Müthing et al., 2002). Viscumin is a 57 kDa heterodimer, comprising of two subunits A and B. The A subunit exerts its toxic effect by disabling ribosomes, thereby interrupting protein production, whereas the B subunit exhibits glycan binding function. The lectin demonstrates picomolar cytotoxicity in vitro and in vivo, and has a recommended dose upper limit of 6 µg/kg in clinical trial subjects (half-life of 13 mins) (Zwierzina et al., 2011).

Another plant lectin that has demonstrated an ability to prevent cell migration and growth (and hence an anti-cancer property) is the *Maackia amurensis* seed lectin, or MASL (Ochoa-Alvarez et al., 2012; Astarita et al., 2012). This lectin is also cytotoxic exhibiting nanomolar potency (~300 nM), and exerts its effects through the binding of podoplanin, an α2,3 sialylated mucin-type transmembrane glycoprotein, that is overexpressed in a variety of human cancers (Kato et al., 2005; Schacht et al., 2005; Shibahara et al., 2006).

The treatment of cell proliferation and differentiation disorders, including, for example cancer, demands the provision of additional molecules that are well tolerated in their hosts and have therapeutic potential.

SUMMARY OF THE INVENTION

The present disclosure is based on the finding that molecules which bind sialic acid also modulate aspects of cell growth and/or cell activity.

Throughout this specification, the terms "comprise", "comprising" and/or "comprises" is/are used to denote that aspects and embodiments of this invention "comprise" a particular feature or features. It should be understood that this/these terms may also encompass aspects and/or embodiments which "consist essentially of" or "consist of" the relevant feature or features.

In a first aspect, there is provided a sialic acid binding molecule for use in a method of modulating cell growth and/or cell activity.

In a second aspect, there is provided a method of modulating cell growth and/or activity, said method comprising contacting a cell with a sialic acid binding molecule. The method may be an in vitro method.

The term "modulating" may embrace any increase or decrease in one or more aspects of cell growth and/or activity. In other words, a sialic acid binding molecule described herein may either inhibit certain aspects of cell growth and/or activity or may induce or stimulate other aspects of cell growth and/or activity.

The terms "growth" and "activity" as applied to cells may embrace processes and/or phenomena associated with one or more of cell proliferation, cell viability, cell migration, cell metabolism, cell differentiation and/or cell morphology/phenotype. The terms "growth" and/or "activity" may further include the response of a cell to certain exogenous and/or endogenous factors or stimuli including, for example, responses to certain compounds of the immune system, cytokines, chemokines and one or more environmental factors (light, temperature, pressure, mechanical stress and the like). Thus, the sialic acid binding molecules disclosed herein may be used to modulate (inhibit, decrease or increase) levels of cell responsiveness.

Given that sialic acid binding molecules have been shown to modulate cell growth and activity (as described above), it will be appreciated that there are also a number of related medical and veterinary applications and uses for these sialic acid binding molecules. For example, a sialic acid binding molecule may be applied to the treatment and/or prevention of diseases in which aberrant cell growth, and/or aberrant cell activity is a factor.

Thus, there is provided a sialic acid binding molecule for use in treating and/or preventing a disease and/or condition caused, contributed to and/or characterised by aberrant cell growth and/or activity.

Further, there is provided use of a sialic acid binding molecule for the manufacture of a medicament for the treatment and/or prevention of a disease and/or condition caused, contributed to and/or characterised by aberrant cell growth and/or activity.

There is also provided a method of treating and/or preventing a disease and/or condition caused, contributed to and/or characterised by aberrant cell growth and/or activity, said method comprising the step of administering a therapeutically effective amount of a sialic acid binding molecule to a subject in need thereof.

Diseases which are caused, contributed to or characterised by aberrant cell growth and/or activity may include, for example cell proliferation and/or differentiation disorders including, those referred to or classified as benign or malignant conditions. For example, the term "cell proliferation and/or differentiation disorders" may include those diseases and/or conditions collectively referred to as "cancer". The term "cancer" may include, but is not limited to, those cancers referred to as forms of breast cancer, bone cancer, brain cancer (gliomas), pancreatic cancer, lung cancer, prostate cancer, skin cancer, ovarian cancer, cervical cancer, head and neck cancers and bowel/colon cancer. The term "cancer" may also include those diseases and/or conditions collectively referred to as "leukaemias" (both chronic and acute) and any cancer affecting a mucosal/mucosal associated surface or tissue.

As such, a sialic acid binding molecule described herein may find application in the treatment and/or prevention of cancer.

Thus, there is provided a sialic acid binding molecule for use in treating and/or preventing cancer.

Further, there is provided use of a sialic acid binding molecule for the manufacture of a medicament for the treatment and/or prevention of cancer.

There is also provided a method of treating and/or preventing cancer, said method comprising the step of administering a therapeutically effective amount of a sialic acid binding molecule to a subject in need thereof.

A subject in need thereof or indeed a subject to be administered a sialic acid binding molecule disclosed herein or a medicament comprising the same, may be any subject suffering (or suspected as suffering) from (i) a cell proliferation and/or differentiation disorder, (ii) cancer, (iii) any other disease and/or condition described herein; or (iv) a disease or condition caused, contributed to or characterised by aberrant cell growth and/or activity. Additionally, or alternatively, any subject may be a subject predisposed or susceptible to (i) a cell proliferation and/or differentiation disorder, (ii) cancer, (iii) any other disease and/or condition described herein; or (iv) a disease or condition caused, contributed to or characterised by aberrant cell growth and/or activity.

It should be understood that the treatment of a cell proliferation and/or differentiation disorder, a cancer or a disease or condition caused or contributed to (or characterised by) aberrant cell growth and/or activity, may involve the use of one or more sialic acid binding molecule(s) of this disclosure to treat, ameliorate or reduce, one or more symptoms of those diseases. By way of example, the symptoms of a disease such as cancer may include, for example, the presence of tumours and/or cell masses. As such, the sialic acid binding molecules described herein may be used to modulate (for example stop, retard, inhibit or reduce) tumour formation and/or the metastasis thereof. The sialic acid binding molecules may also be used to reduce the overall size of a tumour. Certain tumours, including those that are large and/or aggressive, are often easier to surgically remove if they have first been reduced in size. Typically, chemo- and/or radiotherapy based treatments might be used to reduce the size of a tumour but treatments such as this may be replaced by and/or supplemented with sialic acid binding molecule based treatments. As stated, molecules which exhibit sialic acid molecule binding activity exhibit an ability to modulate cell growth and/or activity and therefore, without wishing to be bound by theory, the mechanism underpinning the ability of a sialic acid binding molecule to affect the size of a tumour may be rooted in the cell proliferation, differentiation and/or metabolism modulating effects of the molecule.

In view of the above, the successful treatment of a tumour may therefore be characterised by a reduction in tumour size, a reduction in an observed or detectable/detected level of tumour metastasis, angiogenesis within tumorigenic tissue and/or tissue invasion.

Thus, sialic acid binding molecules may be for use in methods of modulating (for example inhibiting, restricting or reducing) tumour growth, development and/or metastasis in subjects in need thereof. The sialic acid binding molecules described herein may be formulated as compositions for use in modulating tumour growth, development and/or metastasis or used in the manufacture of medicaments for achieving the same. This disclosure also provides a sialic acid binding molecule for use in treating a tumour. Further, described is the use of a sialic acid binding molecule for the manufacture of a medicament for treating a tumour. Also, the disclosure provides a method of treating a tumour, said method comprising administering a sialic acid binding molecule to a subject (or tumorigenic tissue) in need thereof.

As defined earlier, the term "a subject in need thereof" may embrace any subject suspected as having a tumour or diagnosed with a tumour and/or subjects that are identified as being predisposed and/or susceptible to tumours.

The present disclosure therefore provides various applications for sialic acid binding molecules which have been identified as modulators of cell growth and/or activity. Any given sialic acid binding molecule may be identified as a modulator of cell growth and/or activity via the various experiments and assays described in the examples section of this patent application. For example, the cell wound scratch assay is one example of an assay that may be adapted to determine whether any given "test" molecule exhibits the necessary ability to modulate cell growth and/or activity.

Thus, the invention relates to those sialic acid binding molecules which via a cell activity modulation assay (for example a cell wound scratch assay) exhibit an ability to modulate cell growth and/or activity. To this end, the disclosure further provides a method of identifying sialic acid binding molecules for use in methods of modulating cell growth and/or activity or for the various medical and/or veterinary applications described herein, said method comprising subjecting a test compound to an assay capable of reporting an effect of the test compound on cell growth and/or activity, wherein the test compound is a sialic acid binding compound and any if the assay reports that the compound has an effect on any aspect of cell growth and/or activity, the compound may be useful in the treatment and/or prevention of diseases and/or conditions of the type described herein. The assay which is capable of reporting an effect of the test compound on cell growth and/or activity may be a cell wound scratch assay as described herein.

The present disclosure relates to molecules and compounds which exhibit an ability to bind to sialic acid. These molecules may take any form and/or belong to any class of molecule or compound (for example they may be proteins, peptides, carbohydrates, antibodies and the like) and term "sialic acid" embraces all forms of N- or O-substituted neuraminic acid and includes all synthetic, naturally occurring and/or modified forms thereof. Sialic acids may be found as components of cell surface molecules, glycoproteins and glycolipids. Most often, sialic acids are present at the end (terminal regions) of sugar chains connected to cell membranes and/or proteins. For example, some cells of the human upper respiratory tract comprise α-2,6-linked sialic acid receptors and other cells of the upper and lower respiratory tracts comprise α-2,3-linked sialic acid receptors. The sialic acid family encompasses a number (approximately 50) of derivatives that may result from acetylation, glycolylation, lactonisation and methylation at C4, C5, C7, C8 and C9. All such derivatives are to be embraced by the term "sialic acid".

Furthermore, sialic acids are found linked $\alpha(2,3)$ or $\alpha(2,6)$ to Gal and GalNAc or $\alpha(2,8)$ or $\alpha(2,9)$ to another sialic acid. Accordingly, it is important to understand that while the term "sialic acid" is used throughout this specification, it encompasses all derivatives, analogues or variants (either naturally occurring or synthetically generated) thereof as well as monomers, dimers, trimers, oligomers, polymers or concatamers comprising the same.

Thus, a sialic acid binding molecule of this disclosure (and for use as described herein) comprises a moiety which exhibits an affinity for sialic acid—including all forms of sialic acid described above and any form of sialic acid present on the surface of a cell, for example a mammalian cell. These various forms of sialic acid may be collectively referred to as "sialic acid moieties" The sialic acid binding molecules of this disclosure exhibit an affinity for sialic acid and as such they may bind/couple to and/or associate with one or more sialic acid moieties. Thus, the term "sialic acid binding molecule" may further encompass any fragment of a whole sialic acid binding molecule which retains an ability to bind to or otherwise couple or associate with a sialic acid moiety.

Sialic acid binding molecules for use may comprise a single sialic acid binding molecule (a monomeric or monovalent molecule, for example) or, alternatively, two or more sialic acid binding molecules—which two or more molecules may be the same or different—a polymeric or multivalent molecule, for example.

A sialic acid binding molecule for use may comprise, consist essentially of or consist of, one or more of the sialic acid binding molecules known as "carbohydrate binding modules" (CBMs). CBMs suitable for use exhibit an affinity for sialic acid. Carbohydrate binding modules are classified into families and CBMs classed as members of the family 40 CBMs (CBM40) may be useful. The family 40 CBMs embrace molecules of approximately 200 residues and are often found at the N-terminus of GH33 sialidases. They may also be found inserted in the β-propeller of GH33 sialidases.

Exemplary carbohydrate binding modules for use may comprise the sialic acid binding domain of *Vibrio cholerae* NanH sialidase (VcCBM: a CBM40) and/or the equivalent (or homologous) domain from *Streptococcus pneumoniae* NanA sialidase (SpCBM: also a CBM40). Of course, similar or homologous sialic acid binding modules present in other organisms are to be encompassed within the scope of the term "CBM".

An exemplary *Vibrio cholerae* NanH sialidase amino acid sequence is deposited under accession umber A5F7A4 and is reproduced below as SEQ ID NO: 1 (781 amino acids).

```
MRFKNVKKTA LMLAMFGMAT SSNAALFDYN ATGDTEFDSP

AKQGWMQDNT NNGSGVLTNA DGMPAWLVQG IGGRAQWTYS

LSTNQHAQAS SFGWRMTTEM KVLSGGMITN YYANGTQRVL

PIISLDSSGN LVVEFEGQTG RTVLATGTAA TEYHKFELVF

LPGSNPSASF YFDGKLIRDN IQPTASKQNM IVWGNGSSNT

DGVAAYRDIK FEIQGDVIFR GPDRIPSIVA SSVTPGVVTA

FAEKRVGGGD PGALSNTNDI ITRTSRDGGI TWDTELNLTE

QINVSDEFDF SDPRPIYDPS SNTVLVSYAR WPTDAAQNGD

RIKPWMPNGI FYSVYDVASG NWQAPIDVTD QVKERSFQIA

GWGGSELYRR NTSLNSQQDW QSNAKIRIVD GAANQIQVAD

GSRKYVVTLS IDESGGLVAN LNGVSAPIIL QSEHAKVHSF

HDYELQYSAL NHTTTLFVDG QQITTWAGEV SQENNIQFGN

ADAQIDGRLH VQKIVLTQQG HNLVEFDAFY LAQQTPEVEK

DLEKLGWTKI KTGNTMSLYG NASVNPGPGH GITLTRQQNI

SGSQNGRLIY PAIVLDRFFL NVMSIYSDDG GSNWQTGSTL

PIPFRWKSSS ILETLEPSEA DMVELQNGDL LLTARLDFNQ

IVNGVNYSPR QQFLSKDGGI TWSLLEANNA NVFSNISTGT

VDASITRFEQ SDGSHFLLFT NPQGNPAGTN GRQNLGLWFS

FDEGVTWKGP IQLVNGASAY SDIYQLDSEN AIVIVETDNS

NMRILRMPIT LLKQKLTLSQ N
```

The CBM region of SEQ ID NO: 1 is from amino acid residue 25 to 216—this sequence may be SEQ ID NO: 2.

An exemplary *Streptococcus pneumoniae* NanA sialidase amino acid sequence has been deposited under accession number P62575 and is reproduced below as SEQ ID NO: 3 (1035 amino acids).

```
MSYFRNRDID IERNSMNRSV QERKCRYSIR KLSVGAVSMI

VGAVVFGTSP VLAQEGASEQ PLANETQLSG ESSTLTDTEK

SQPSSETELS GNKQEQERKD KQEEKIPRDY YARDLENVET

VIEKEDVETN ASNGQRVDLS SELDKLKKLE NATVHMEFKP

DAKAPAFYNL FSVSSATKKD EYFTMAVYNN TATLEGRGSD

GKQFYNNYND APLKVKPGQW NSVTFTVEKP TAELPKGRVR

LYVNGVLSRT SLRSGNFIKD MPDVTHVQIG ATKRANNTVW

GSNLQIRNLT VYNRALTPEE VQKRSQLFKR SDLEKKLPEG

AALTEKTDIF ESGRNGKPNK DGIKSYRIPA LLKTDKGTLI

AGADERRLHS SDWGDIGMVI RRSEDNGKTW GDRVTITNLR

DNPKASDPSI GSPVNIDMVL VQDPETKRIF SIYDMFPEGK

GIFGMSSQKE EAYKKIDGKT YQILYREGEK GAYTIRENGT

VYTPDGKATD YRVVVDPVKP AYSDKGDLYK GNQLLGNIYF

TTNKTSPFRI AKDSYLWMSY SDDDGKTWSA PQDITPMVKA

DWMKFLGVGP GTGIVLRNGP HKGRILIPVY TTNNVSHLNG

SQSSRIIYSD DHGKTWHAGE AVNDNRQVDG QKIHSSTMNN

RRAQNTESTV VQLNNGDVKL FMRGLTGDLQ VATSKDGGVT

WEKDIKRYPQ VKDVYVQMSA IHTMHEGKEY IILSNAGGPK

RENGMVHLAR VEENGELTWL KHNPIQKGEF AYNSLQELGN

GEYGILYEHT EKGQNAYTLS FRKFNWDFLS KDLISPTEAK

VKRTREMGKG VIGLEFDSEV LVNKAPTLQL ANGKTARFMT

QYDTKTLLFT VDSEDMGQKV TGLAEGAIES MHNLPVSVAG

TKLSNGMNGS EAAVHEVPEY TGPLGTSGEE PAPTVEKPEY

TGPLGTSGEE PAPTVEKPEY TGPLGTAGEE AAPTVEKPEF

TGGVNGTEPA VHEIAEYKGS DSLVTLTTKE DYTYKAPLAQ

QALPETGNKE SDLLASLGLT AFFLGLFTLG KKREQ
```

The CBM region of SEQ ID NO: 3 is from amino acid residue 121 to 305—this sequence may be SEQ ID NO: 4.

Thus, CBMs for use as sialic acid binding molecules in the various aspects and embodiments of this disclosure may comprise a protein or peptide having the sequence of SEQ ID NO: 1 or 2 or a sialic acid binding fragment thereof.

A useful sialic acid binding molecule may comprise a proteinaceous moiety encoded by the sialic acid binding domain of the nanH gene (encoding sialidase) of *V. cholerae* (as provided by SEQ ID NO: 1) or an equivalent or homologous gene present in another organism (for example the equivalent/homologous nanA sialidase gene of *S. pneumoniae*: see SEQ ID NO: 3).

A sialic acid binding molecule for use may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase molecule of SEQ ID NOS: 1 and 2. For example, a sialic acid binding molecule for use may comprise a peptide having a sequence corresponding to residue 25 to about residue 216 of SEQ ID NO: 1 above.

A further suitable sialic acid binding molecule may comprise a protein or peptide having the sequence of SEQ ID NO: 3 or 4 or a sialic acid binding fragment thereof. For example, a useful sialic acid binding molecule may comprise a proteinaceous moiety encoded by the sialic acid binding domain of the *Streptococcus pneumoniae* nanA gene (encoding sialidase). For example, a sialic acid binding molecule for use may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase molecule of SEQ ID NOS: 3 and 4. For example, a sialic acid binding molecule for use may comprise a peptide having a sequence corresponding to residue 121 to about residue 305 of SEQ ID NO: 3 above.

A sialic acid binding molecule for use may comprise one or more CBMs. For example, suitable sialic acid binding molecules may comprise single CBMs—for example, a single VcCBM or a single SpCBM. Alternatively, a sialic acid binding molecule for use may comprise a plurality or multiple (i.e. two or more) CBMs. Sialic acid binding molecules which comprise a plurality of CBMs may be termed "multivalent sialic acid binding molecules" or "multivalent CBMs". A multivalent CBM may, for example, comprise two or more VcCBMs or two or more SpCBMs. A multivalent CBM may comprise a mixture of different CBMs, for example one or more VcCBMs with one or more SpCBMs.

For example, multivalent CBM molecules, (for example a Vc4CBM molecule) may be prepared as constructs comprising multiple CBMs linked by amino acid/peptide linkers. Each CBM (for example VcCBM) may be linked to another by, for example, peptides comprising 5, 10 or 15 amino acids. By way of example any one or more of the following peptides may be used to link two or more CBMs to produce a multivalent CBM:

| (i) | 5 amino acid linkers: | ALNGS (SEQ ID NO: 7)<br>LQALG (SEQ ID NO: 8)<br>GGNSG (SEQ ID NO: 9) |
|---|---|---|
| (ii) | 10 amino acid linkers: | ALNGSGGGSG (SEQ ID NO: 10)<br>LQALGGGGSL (SEQ ID NO: 11) |
| (iii) | 15 amino acid linkers: | ALNGSGGGSGGGGSG (SEQ ID NO: 12). |

Thus, the various aspects and embodiments of this invention (uses, sialic acid binding molecules for use, methods and medicaments) may exploit sialic acid binding molecules which comprise, consist of or consist essentially of sialic acid binding molecules selected from the group consisting of:

(i) one or more VcCBM(s);
(ii) one or more SpCBM(s); and
(iii) a multivalent CBM.

The sialic acid binding molecules for use may further comprise an oligomerisation domain. Suitable oligomerisation domains may exhibit an ability to self-associate to form multimer structures, for example trimers. An oligomerisation domain for use may comprise any molecule with the above mentioned oligomerisation properties or any functional fragment thereof. For example, one or more (for example two) sialic acid binding molecules (for example CBMs) may be bound, coupled or fused to an oligomerisation domain—the resulting sialic acid binding molecule: oligomerisation domain "fusion" may then be used (with one or more other such "fusions") as a molecule for modulating cell growth and/or activity and/or for treating or preventing any of the diseases and/or conditions disclosed herein.

Suitable oligomerisation domains may be derived from, for example, *Pseudomonas aeruginosa* pseudaminidase. An exemplary *Pseudomonas aeruginosa* pseudaminidase sequence amino acid sequence has been deposited under accession number PAO579 and is reproduced below as SEQ ID NO: 5 (438 amino acids).

```
MNTYFDIPHR LVGKALYESY YDHFGQMDIL SDGSLYLIYR

RATEHVGGSD GRVVFSKLEG GIWSAPTIVA QAGGQDFRDV

AGGTMPSGRI VAASTVYETG EVKVYVSDDS GVTWVHKFTL

ARGGADYNFA HGKSFQVGAR YVIPLYAATG VNYELKWLES

SDGGETWGEG STIYSGNTPY NETSYLPVGD GVILAVARVG

SGAGGALRQF ISLDDGGTWT DQGNVTAQNG DSTDILVAPS

LSYIYSEGGT PHVVLLYTNR TTHFCYYRTI LLAKAVAGSS

GWTERVPVYS APAASGYTSQ VVLGGRRILG NLFRETSSTT

SGAYQFEVYL GGVPDFESDW FSVSSNSLYT LSHGLQRSPR

RVVVEFARSS SPSTWNIVMP SYFNDGGHKG SGAQVEVGSL

NIRLGTGAAV WGTGYFGGID NSATTRFATG YYRVRAWI
```

The oligomerisation domain of SEQ ID NO: 5 is from amino acid residue 333 to 438—this sequence may be SEQ ID NO: 6.

Thus an oligomerisation domain for use may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD) provided by SEQ ID NO: 5. For example, a useful sialic acid binding molecule may exploit an oligomerisation domain comprising residues 333 to 438 of SEQ ID NO: 6.

Figure 1:
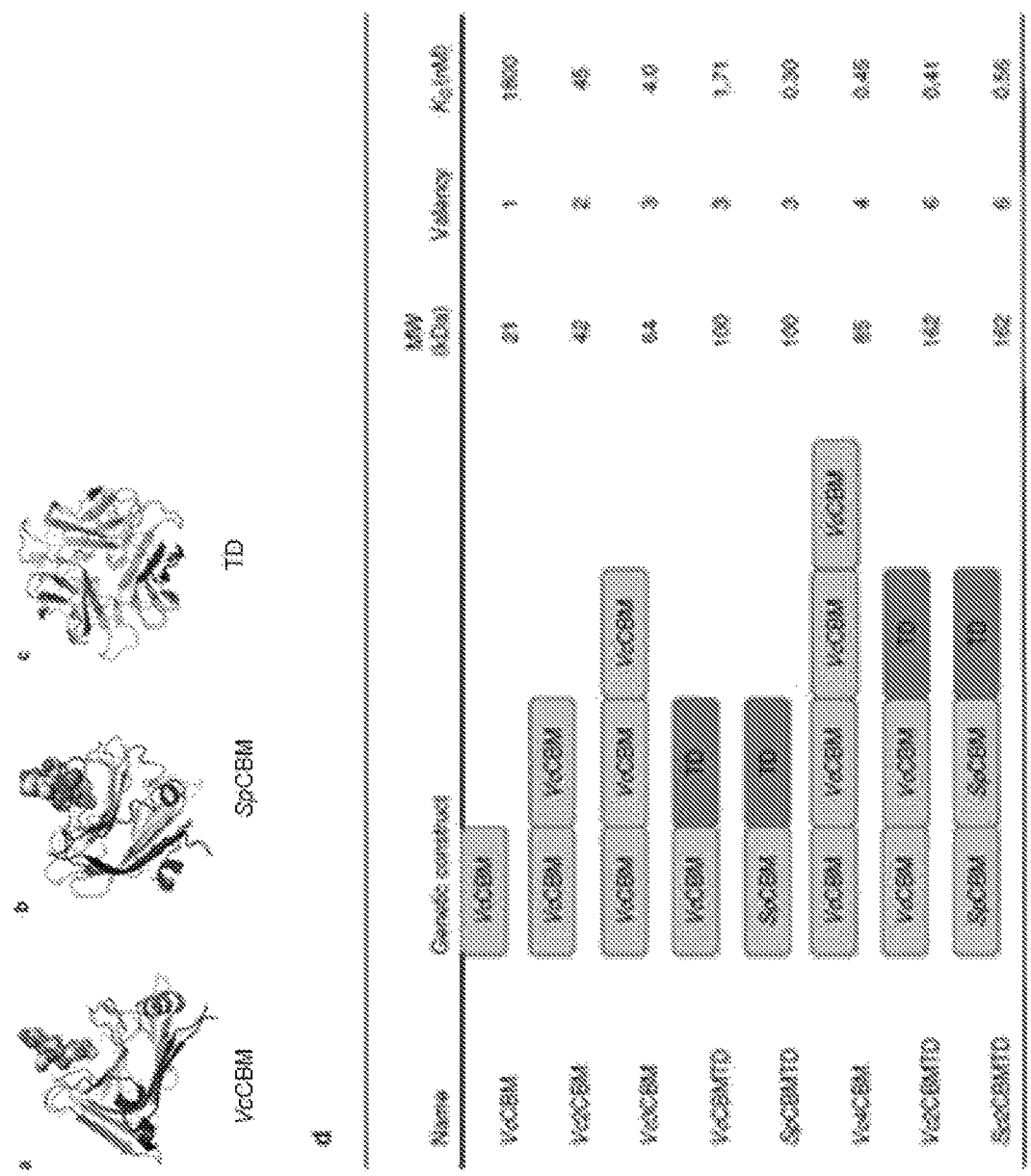

A sialic acid binding molecule for use may comprise one or more of the CBM based molecules presented in FIG. 1. For example, a suitable sialic acid binding molecule may comprise (consist essentially of, or consist of) two or more VcCBMs optionally fused, bound or conjugated to an oligomerisation domain (such as a PaTD or oligomerisation fragment thereof). The sialic acid binding molecule may comprise, consist or consist essentially of two fused (or bound) VcCBMs which are in turn fused to an oligomerisation domain (see, for example, molecule Vc2CBMTD shown in FIG. 1).

Other sialic acid binding domains for use may comprise two or more SpCBMs optionally fused, bound or conjugated to an oligomerisation domain (such as a PaTD or an oligomerisation fragment thereof). Sialic acid binding molecules for use may comprise, consist or consist essentially of two fused (or bound) SpCBMs which are in turn fused to an oligomerisation domain (see, for example, molecule Sp2CBMTD shown in FIG. 1).

Thus, this disclosure provides:
(i) a CBM for use in a method of modulating cell growth and/or cell activity; said method comprising contacting a cell with a CBM;
(ii) a method of modulating cell growth and/or activity, said method comprising contacting a cell with a CBM. The method may be an in vitro method;
(iii) a CBM for use in treating and/or preventing a disease and/or condition caused, contributed to and/or characterised by aberrant cell growth and/or proliferation;
(iv) use of a CBM for the manufacture of a medicament for the treatment and/or prevention of diseases and/or conditions caused, contributed to and/or characterised by aberrant cell growth and/or proliferation;
(v) a method of treating and/or preventing a disease and/or condition caused, contributed to and/or characterised by aberrant cell growth and/or proliferation, said method comprising the step of administering a therapeutically effective amount of a sialic acid binding molecule to a subject in need thereof;
(vi) a CBM for use in treating and/or preventing cancer;
(vii) use of a CBM for the manufacture of a medicament for the treatment and/or prevention of cancer; and
(viii) a method of treating and/or preventing cancer, said method comprising the step of administering a therapeutically effective amount of a sialic acid binding molecule to a subject in need thereof.

In any one of embodiments (i) to (viii) above, the CBM may be a multivalent CBM comprising two or more family 40 CBMs. For example, in any one of embodiments (i) to (viii) above, the CBM may comprise (consist essentially of, or consist of) two or more VcCBMs and/or SpCBMs optionally fused, bound or conjugated to an oligomerisation domain (such as a PaTD or oligomerisation fragment thereof). The sialic acid binding molecule may comprise, consist or consist essentially of two fused (or bound) VcCBMs or two fused (or bound) SpCBMs which are in turn fused to an oligomerisation domain (see, for example, molecule Vc2CBMTD and Sp2CBMTD shown in FIG. 1).

In view of the above, this disclosure provides:
(i) the sialic acid binding domain of *Vibrio cholerae* NanH sialidase (VcCBM) and/or the sialic acid binding domain of *Streptococcus pneumoniae* NanA sialidase (SpCBM) for use in a method of modulating cell growth and/or cell activity; said method comprising contacting a cell with the sialic acid binding domain of *Vibrio cholerae* NanH sialidase (VcCBM) and/or the sialic acid binding domain of *Streptococcus pneumoniae* NanA sialidase (SpCBM);
(ii) A method of modulating cell growth and/or activity, said method comprising contacting a cell with the sialic acid binding domain of *Vibrio cholerae* NanH sialidase (VcCBM) and/or the sialic acid binding domain of *Streptococcus pneumoniae* NanA sialidase (SpCBM). The method may be an in vitro method;
(iii) The sialic acid binding domain of *Vibrio cholerae* NanH sialidase (VcCBM) and/or the sialic acid binding domain of *Streptococcus pneumoniae* NanA sialidase (SpCBM) for use in treating and/or preventing a disease and/or condition caused, contributed to and/or characterised by aberrant cell growth and/or proliferation;
(iv) use of the sialic acid binding domain of *Vibrio cholerae* NanH sialidase (VcCBM) and/or the sialic acid binding domain of *Streptococcus pneumoniae* NanA sialidase (SpCBM) for the manufacture of a medicament for the treatment and/or prevention of diseases and/or conditions caused, contributed to and/or characterised by aberrant cell growth and/or proliferation;
(v) a method of treating and/or preventing a disease and/or condition caused, contributed to and/or characterised by aberrant cell growth and/or proliferation, said method comprising the step of administering a therapeutically effective amount of the sialic acid binding domain of *Vibrio cholerae* NanH sialidase (VcCBM) and/or the sialic acid binding domain of *Streptococcus pneumoniae* NanA sialidase (SpCBM) to a subject in need thereof;
(vi) the sialic acid binding domain of *Vibrio cholerae* NanH sialidase (VcCBM) and/or the sialic acid binding domain of *Streptococcus pneumoniae* NanA sialidase (SpCBM) for use in treating and/or preventing cancer;
(vii) use of the sialic acid binding domain of *Vibrio cholerae* NanH sialidase (VcCBM) and/or the sialic acid binding domain of *Streptococcus pneumoniae* NanA sialidase (SpCBM) for the manufacture of a medicament for the treatment and/or prevention of cancer; and
(viii) a method of treating and/or preventing cancer, said method comprising the step of administering a therapeutically effective amount of the sialic acid binding domain of *Vibrio cholerae* NanH sialidase (VcCBM) and/or the sialic acid binding domain of *Streptococcus pneumoniae* NanA sialidase (SpCBM) to a subject in need thereof.

Additionally, the disclosure provides:
(i) A CBM (as described herein) and/or the sialic acid binding domain of *Vibrio cholerae* NanH sialidase (VcCBM) and/or the sialic acid binding domain of *Streptococcus pneumoniae* NanA sialidase (SpCBM) for use in (a method of) modulating tumour growth;
(ii) Use of a CBM (as described herein) and/or the sialic acid binding domain of *Vibrio cholerae* NanH sialidase (VcCBM) and/or the sialic acid binding domain of *Streptococcus pneumoniae* NanA sialidase (SpCBM) in the manufacture of a medicament for use in modulating tumour growth; and
(iii) A method of modulating tumour growth, said method comprising administering a therapeutically effective or tumour growth modulating amount of a CBM (as described herein) and/or the sialic acid binding domain of *Vibrio cholerae* NanH sialidase (VcCBM) and/or the sialic acid binding domain of *Streptococcus pneumoniae* NanA sialidase (SpCBM), to a subject in need thereof.

Molecules which bind sialic acid and in particular sialic acid which is part of a cell bound receptor, may find further application as moieties which may be conjugated, bound or joined to or associated with, other entities for the purpose of targeting or delivering that entity to some tissue or cell. Molecules of this type may be otherwise known as "therapeutic warheads" or "conjugates". Without wishing to be bound by theory, the presence of sialic acid in certain cell receptors and membrane bound molecules, may allow the sialic acid binding molecule to be exploited as a means to deliver conjugated heterologous molecules (that is a molecule distinct from and different to the sialic acid binding molecule) to said cells or tissues comprising said cells. Thus, conjugated sialic acid binding molecules may be useful in the treatment of cancer, where sialic acid binding molecules (with affinity for sialic acids expressed on cancerous cells and/or tumours) may be used to direct therapeutic and/or cytotoxic moieties thereto.

By way of example, a sialic acid binding molecule as described herein (including any of the CBM based molecules) may be conjugated to moieties which are, for example, therapeutic and/or cytotoxic. Thus, the disclosure relates to sialic acid binding molecule conjugates.

Sialic acid binding molecule conjugates may comprise a sialic acid binding molecule of this disclosure conjugated (joined, bound or otherwise associated with) to a heterologous moiety. The heterologous moiety may comprise a therapeutic and/or cytotoxic moiety which may be conjugated to some part of the sialic acid binding molecule. For example, the heterologous moiety may be conjugated to one or both ends of the sialic acid binding molecule. The heterologous moiety may be additionally or alternately conjugated (or even fused) to an internal portion of the sialic acid binding molecule. It will be appreciated that however the heterologous moiety is to be conjugated to the sialic acid binding molecule, the moiety (nor its conjugation) should not (substantially) interfere with or ablate or reduce the sialic acid binding property of the sialic acid binding molecule.

As stated, the heterologous moiety may be a drug useful in the treatment of a disease which affects a cell or tissue comprising sialic acid. For example, the drug may be a chemotherapeutic drug for use in the treatment of cancer and the like. The heterologous moiety may be a cytotoxic moiety capable of killing or inducing apoptosis in, a cell. The heterologous moiety may comprise a molecule which is able to recruit specific cells to or into a particular tissue. For example, the heterologous moiety may be, for example, a T cell receptor (TCR) which may be used as a means to recruit T cells to, for example a tumour or cancerous tissue.

The present disclosure may provide compositions for use in the various uses, medicaments and methods described herein. As such, any of the sialic acid binding molecule(s) described herein may be formulated for use. For convenience, and with reference to the section below describing compositions, formulations and the like it should be noted that both sialic acid binding molecules as described herein and any conjugates comprising the same (for example sialic acid binding molecule:drug conjugates/fusions) shall be included under the general term "sialic acid binding molecule".

A sialic acid binding molecule (or molecules) may be formulated for use and as a therapeutic or pharmaceutical composition. The various compositions may comprise one or more of the sialic acid binding molecules described herein and any given treatment may require the administration (together, concurrently or separately) of one or more of these compositions.

The various sialic acid binding molecules described herein may be formulated for enteral (including oral), parenteral and/or topical administration and one of skill will appreciate that the precise formulation may vary depending on the route of administration.

Pharmaceutical compositions according to the present invention may be prepared conventionally, comprising substances that are customarily used in pharmaceuticals and as described in, for example, Remington’s The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

A therapeutic or pharmaceutical composition of this disclosure (that is a composition comprising a sialic acid binding molecule and for use in any of the medicaments or methods described herein—including the methods of or medicaments for, modulating cell growth and/or activity and/or treating cancer) may be formulated together with one or more pharmaceutically acceptable excipients, carriers, adjuvants and buffers. The compositions can be administered, e.g. orally (including mucosally), parentally, enterally, intramuscularly, subcutaneously, intravenously or via any other routes useful to achieve the desired effect (in this case effects which include, modulation of cell growth/activity, treatment or prevention of diseases/conditions associated with the same and/or cancer and/or modulation of tumour growth). As stated, depending on the chosen route of administration, the exact composition of the formulation may vary.

A therapeutic or pharmaceutical formulation comprising a sialic acid binding molecule and for administration to a subject may be coated, encapsulated or enveloped in a material which protects the sialic acid binding molecule from the action of enzymes, acids and other natural compounds/conditions (including, for example, compounds (including antibodies), cells and processes of the immune system) which may inactivate or denature the compound and/or its sialic acid binding properties.

Among the various standard and conventional excipients that may be available for use in compositions comprising sialic acid binding molecules, are those pharmaceutically acceptable organic or inorganic carrier substances which are suitable for parenteral, enteral, oral (including mucosal) and other routes of administration that do not deleteriously react with the sialic acid binding molecule(s).

Where the sialic acid binding molecules are to be formulated for parental administration, the compositions may be sterile.

The composition may comprise an oil-based or aqueous solution, a suspension and/or an emulsion.

In other embodiments, the composition may take the form of an implant, such as for example a (dissolvable or biodegradable) film, pessary or implant (including suppositories).

The pharmaceutical preparations comprising sialic acid binding molecules may be mixed with stabilizers, wetting agents, emulsifiers, salts (for use in influencing osmotic pressure), buffers and/or other substances that do not react deleteriously with the active compounds.

One or more of the sialic acid binding molecules described herein may be formulated for and administered, orally. As stated, oral administration would include mucosal administration which would itself would include administration intranasally and/or by inhalation.

Compositions for use may include solid dosage forms which are suitable for oral administration. These may include, for example capsules, tablets, pills, powders, and granules. In any given solid dosage form, the sialic acid binding molecule (or any conjugate comprising the same) may be admixed with at least one inert pharmaceutically-acceptable excipient. Examples of suitable excipients will be known to one of skill in this field but may include, for example fillers or extenders, humectants, wetting agents, binders, disintegrating agents, solution retarders, absorption accelerators, adsorbents, lubricants or mixtures thereof. A tablet, pill or capsule may further comprise a buffering agent. Solid dosage forms such as tablets, dragees, capsules, pills and/or granules also can be prepared with coatings and shells, such as coatings which protect against the gastrointestinal environment and/or stomach acid.

A solid dosage form may contain opacifying agents, and can also be formulated so as to ensure the delayed release of the active agent (in this case the sialic acid binding molecule or a conjugate comprising the same) in or to a specific part of the intestinal tract.

Solid compositions for oral administration can be formulated in a unit dosage form, each dosage containing an appropriate dose of the sialic acid binding molecule (or conjugate comprising the same). The exact amount of sialic acid binding molecule (or conjugate comprising the same) contained within any given solid dosage form will vary depending on the intended use. a solid composition may contain a "unit dose"—a unit dose containing a quantity of sialic acid binding molecule (or conjugate containing the same) calculated to produce the desired effect (for example modulation of cell growth and/or activity) over the course of a treatment period.

Liquid dosage forms for oral administration may (as stated) include emulsions, solutions, suspensions, syrups, and elixirs. In addition to the compound or composition, the liquid dosage forms may contain inert diluents commonly used in the art, such as water or other solvents, solubilizing agents and emulsifiers.

The sialic acid binding molecules may be used in any suitable amount. As stated, the sialic acid binding molecules may be formulated for oral, mucosal or parenteral administration and as such, the precise formulation may depend on the intended route of administration. The amount of sialic acid binding molecule present in any given dose may be in the region of 0.1 μg-1000 μg. For example, amounts of about 0.1 μg, 0.2 μg, 0.3 μg, 0.4 μg, 0.5 μg, 1 μg, 10 μg, 20 μg, 25 μg, 50 μg, 100 μg, 200 μg, 300 μg, 400 μg, 500 μg, 600 μg, 700 μg, 800 μg or 900 μg. The selected amount of sialic acid binding molecule may be formulated in a specific volume of a pharmaceutically acceptable excipient, diluent and/or buffer. The volume of excipient, diluent or buffer may be about 10 μl to 5 ml. For example, the required amount of sialic acid binding molecule (CBM) may be combined (or formulated) with about 15 μl, 20 μl, 25 μl, 30 μl, 35 μl, 40 μl, 45 μl, 50 μl, 55 μl, 60 μl, 65 μl, 70 μl, 75 μl, 80 μl, 85 μl, 90 μl, 95 μl, 100 μl, 200 μl, 250 μl, 300 μl, 400 μl, 500 μl, 600 μl, 700 μl, 800 μl, 900 μl, 1 ml, 2 ml, 3 ml or 4 ml. For example, an amount of 100 μg sialic acid binding molecule may be combined with about 250 μl of excipient to yield a final concentration of sialic acid concentration of 400 μg/ml. Doses at concentrations of about 0.1 μg/ml-1 mg/ml may be used including, for example, doses at 5 μg/ml, 10 μg/ml, 20 μg/ml, 25 μg/ml, 50 μg/ml, 100 μg/ml, 200 μg/ml, 300 μg/ml, 500 μg/ml, 600 μg/ml, 700 μg/ml, 800 μg/ml or 900 μg/ml.

In use, a dose of a sialic acid binding molecule, administered as part of the treatment and/or prevention of a cell proliferation and/or differentiation disorder (for example cancer), may be administered multiple times over a number of days or weeks. For example, after an initial (or first) administration, a dose of a sialic acid binding molecule may be administered again at about (+/−1 or 2 days) 3, 4, 5, 6, 7, 17, 21, 28 and/or 35 days later. On any given day, a specific dose of a sialic acid binding molecule may be administered 1, 2, 3 or more times. Each time, the sialic acid binding molecule may be administered (by whatever route is considered best to affect a suitable treatment or to induce prophylaxis against the development of a cell proliferation and/or differentiation disorder.

DETAILED DESCRIPTION

The present invention will now be described in detail by reference to the following Figures which show:

FIG. 1. Building blocks of the multivalent CBM forms and their affinities for sialic acid. a, VcCBM, residues 25-216 of the *V. cholerae* sialidase (PDB:1w0p) with α-2,3-sialyllactose drawn as spheres. b, SpCBM, residues 121-305 of *S. pneumoniae* NanA sialidase with α-2,3-sialyllactose (PDB:4c1w). c, TD, the trimerisation domain, residues 333-438, of the *P. aeruginosa* pseudaminidase (PDB:2w38) in rainbow colors; the other two monomers in single colors. d, Multivalent forms: their molecular weights, valencies and binding affinities for α2,3-sialyllactose as determined by surface plasmon resonance (SPR) at 25° C. ($K_D$ values for VcCBM, Vc2CBM and Vc3CBM had been reported previously (Connaris et al, 2009)). Tandem repeat CBMs, and oligomeric CBMs fused to TD are linked by a 5-amino linker (details in Connaris et al, 2014).

FIG. 2: CBM dose analysis on A549 human lung carcinoma cells. Left panel: 10-fold serially diluted single dose (i.e. 400 μg to 0.04 μg per well) of Vc2CBMTD (top panel), and of Sp2CBMTD (bottom panel). The right panel is identical to the left, except that cells are given CBMs twice over three days. CBMs were diluted in serum-free DMEM and incubated with cells for 3 h before removing and replaced with DMEM/5% FCS for cell maintenance. Mock wells represent cells that are given PBS only in DMEM/5% FCS.

FIG. 3: Wound healing assay on A549 human lung carcinoma cells. Cells were scratched to create an artificial wound before treatment with PBS (A), 100 μg/ml Sp2CBMTD (B), or 100 μg/ml Vc2CBMTD (C), in serum-free DMEM. Cells were left for 24 h, followed by actin staining to visualise cell cytoskeleton.

FIG. 4: (A) The MTT assay absorbance indicating the metabolic activity of A549 human lung carcinoma cells after treatment with either 50 μg/ml of monomeric CBM-like domain (TcTs), or 5 μg/ml of hexameric CBMs (Vc2CBMTD or Sp2CBMTD) resuspended in serum-free DMEM or in serum-free DMEM with 2 mM sialyllactose (+Sia) for 24 h at 37 deg C., 5% $CO_2$. (B) Cell morphology of treated vs PBS only cells (control) after 24 h.

FIG. 5: A. Scratch assay data from a human lung cancer cell line (A549) using mCBM40s. Hexameric Vc2CBMTD and Sp2CBMTD were tested at 100 μg in a 250 μL volume representing a concentration of 400 μg/ml. Phase contrast images represent the wound healing assay after 1 h and 72 h, after cells were treated with PBS, Vc2CBMTD, or Sp2CBMTD, in serum-free DMEM. Yellow bar at bottom of each image indicate diameter of 400 μm. B. Graphs representing the percentage of wound healing (ii), and rate of wound closure (ii) for A549 cells in the absence and presence of mCBM40s after 72 h. Dunnett's multiple comparison test was performed on the data. **** represents a statistical significance $p<0.0001$.

FIG. 6: A. Scratch assay data from a human cervical cancer cell line (HeLa) using mCBM40s. Hexameric Vc2CBMTD and Sp2CBMTD were tested at 100 μg in a 250 μL volume representing a concentration of 400 μg/ml. Fluorescent images represent the wound healing assay after 1 h and 72 h, after cells were treated with PBS, Vc2CBMTD, or Sp2CBMTD, in serum-free DMEM. Yellow bar at bottom of each image indicate diameter of 400 μm. B. Graphs representing the percentage of wound healing (ii), and rate of wound closure (ii) for HeLa cells in the absence and presence of mCBM40s after 72 h. Dunnett's multiple comparison test was performed on the data. **** represents a statistical significance p<0.0001.

FIG. 7: Scratch assay data for lung (A549), cervical (HeLa), breast (MDA.MB.231 and MCF-7) and colon (SW480 and SW620) cancer cell types in the presence and absence of Sp2CBMTD 100 µg (400 µg/mL). (a) Graph representing percentage of A549 cell wound closure in the presence and absence of Sp2CBMTD 100 µg after 72 hrs. (b) Graph representing percentage of HeLa cell wound closure in the presence and absence of Sp2CBMTD 100 µg after 72 hrs. (c). Graph representing percentage of MDA.MB.231 cell wound closure in the presence and absence of Sp2CBMTD 100 µg after 72 hrs. (d). Graph representing percentage of MCF-7 cell wound closure in the presence and absence of Sp2CBMTD 100 µg after 72 hrs. (e). Graph representing percentage of SW620 cell wound closure in the presence and absence of Sp2CBMTD 100 µg after 72 hrs. (f). Graph representing percentage of SW480 cell wound closure in the presence and absence of Sp2CBMTD 100 µg after 72 hrs. All data normalised to control. Unpaired t test performed on data, statistical significance (p) was reported between control and Sp2CBMTD (p=0.0001) highlighted by ****.

Figure 8:
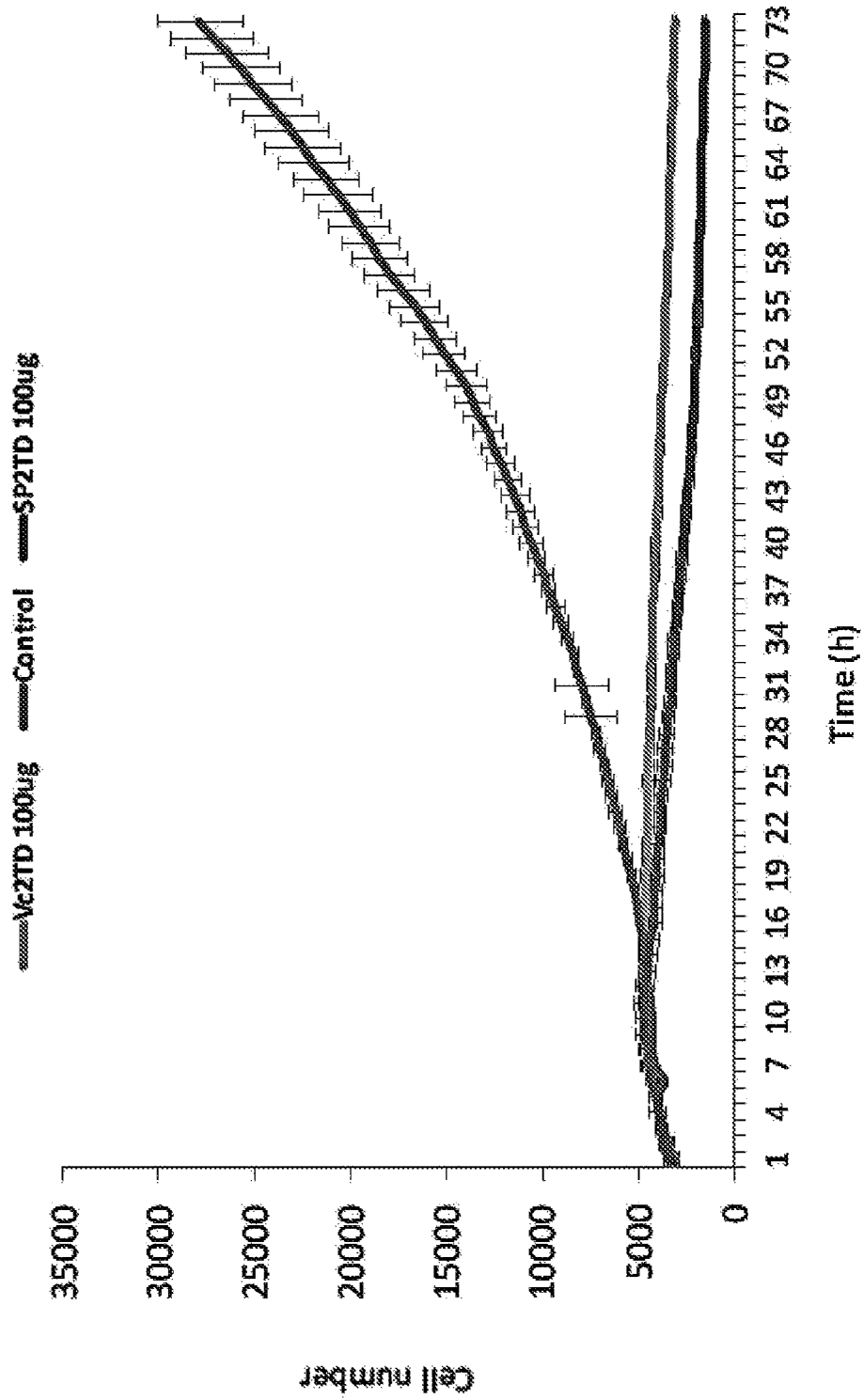

FIG. 8: Cell proliferation of HeLa cells in the presence and absence of hexameric CBM40s. Graph depicts cell number against time (h). Vc2CBMTD and Sp2CBMTD were tested at 100 µg in a 250 µL volume representing a concentration of 400 µg/ml. PBS served as control.

Figure 9A:
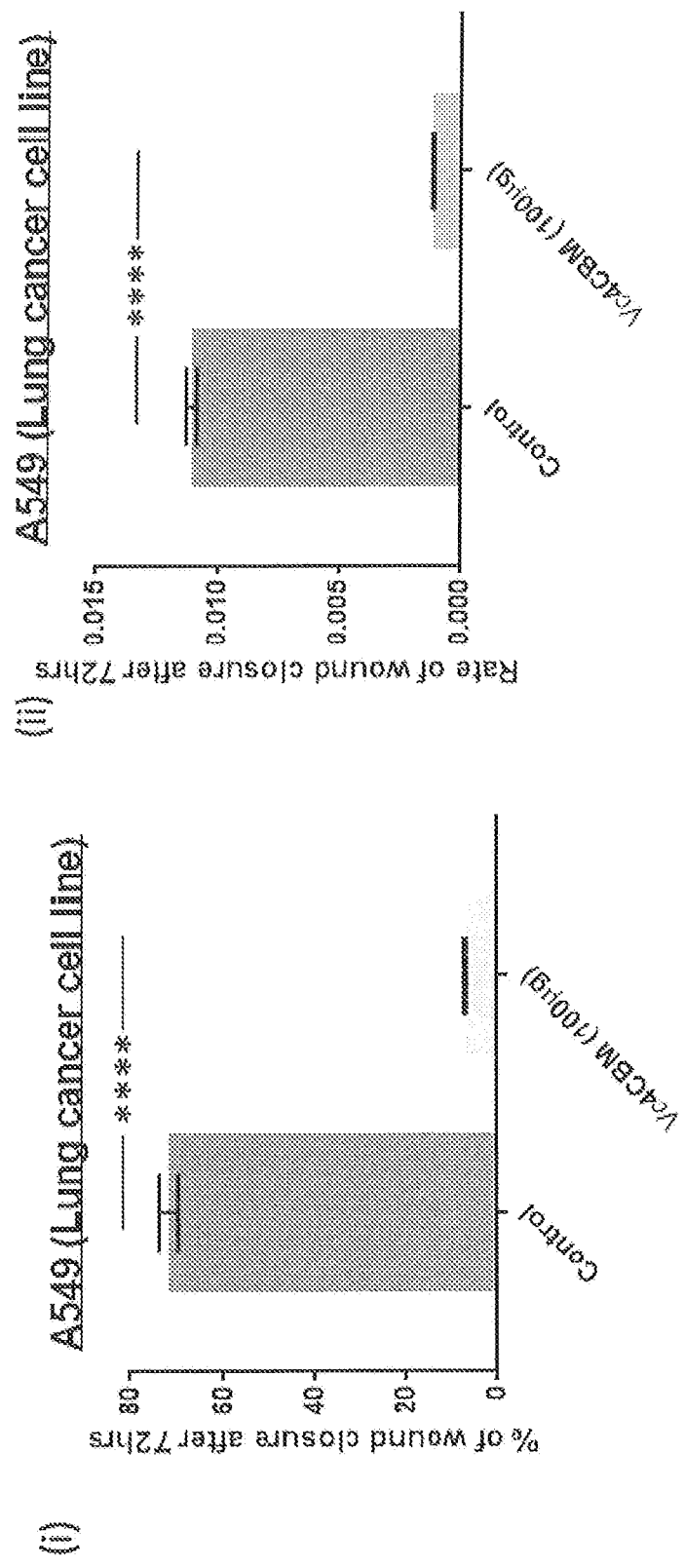
Figure 9B:
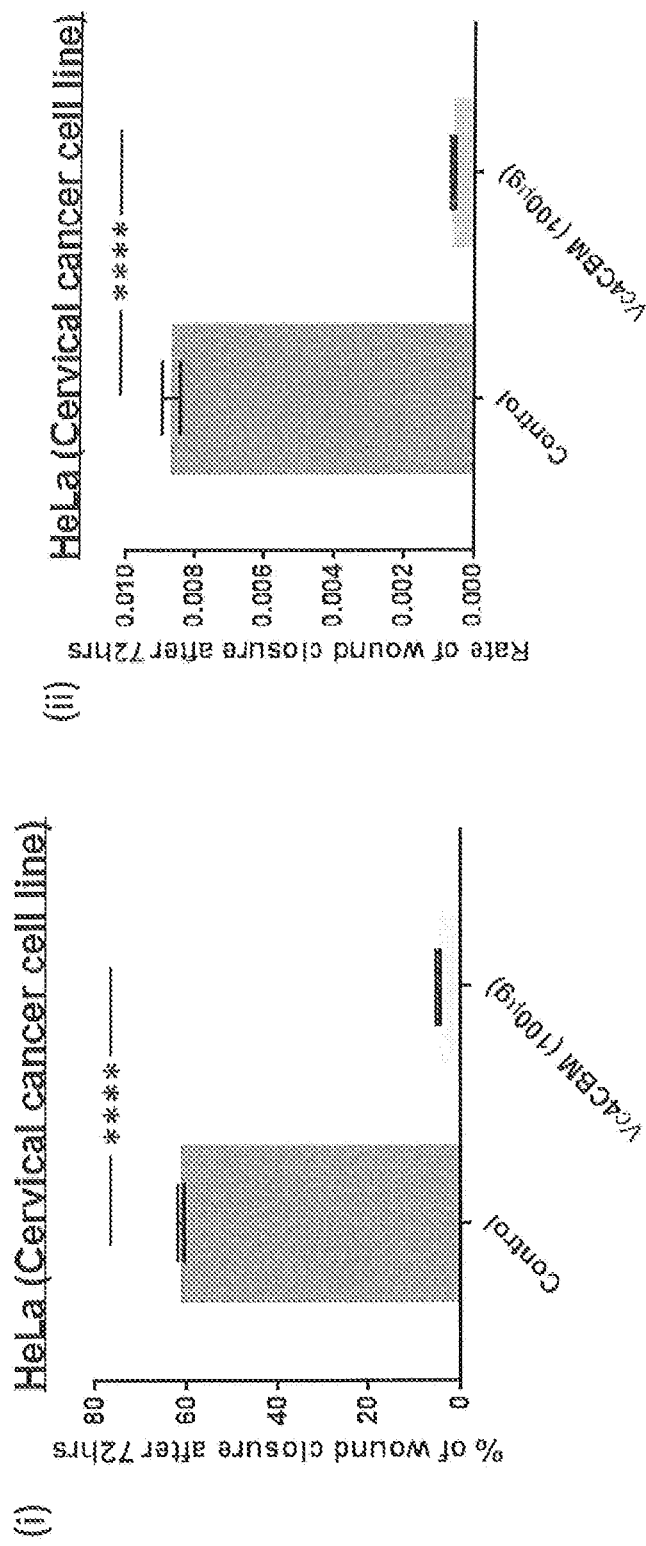

FIG. 9: Scratch assay data from a lung cancer cell line (A549) and a cervical cancer cell line (HeLa) using a tetrameric CBM40. Vc4CBM tested at 100 µg in a 250 µL volume representing a concentration of 400 µg/mL. A. Graphs representing percentage (i), and rate (ii), of A549 cell wound closure in the presence and absence of Vc4CBM after 72 hrs. B. Graph representing percentage (i) and rate (ii) of HeLa cell wound closure in the presence and absence of Vc4CBM also after 72 hrs. Unpaired t test was performed on all data with statistical significance (p) reported between control and Vc4CBM (p=0.0001) as highlighted by control and Vc4CBM highlighted by ****.

Figure 10A:
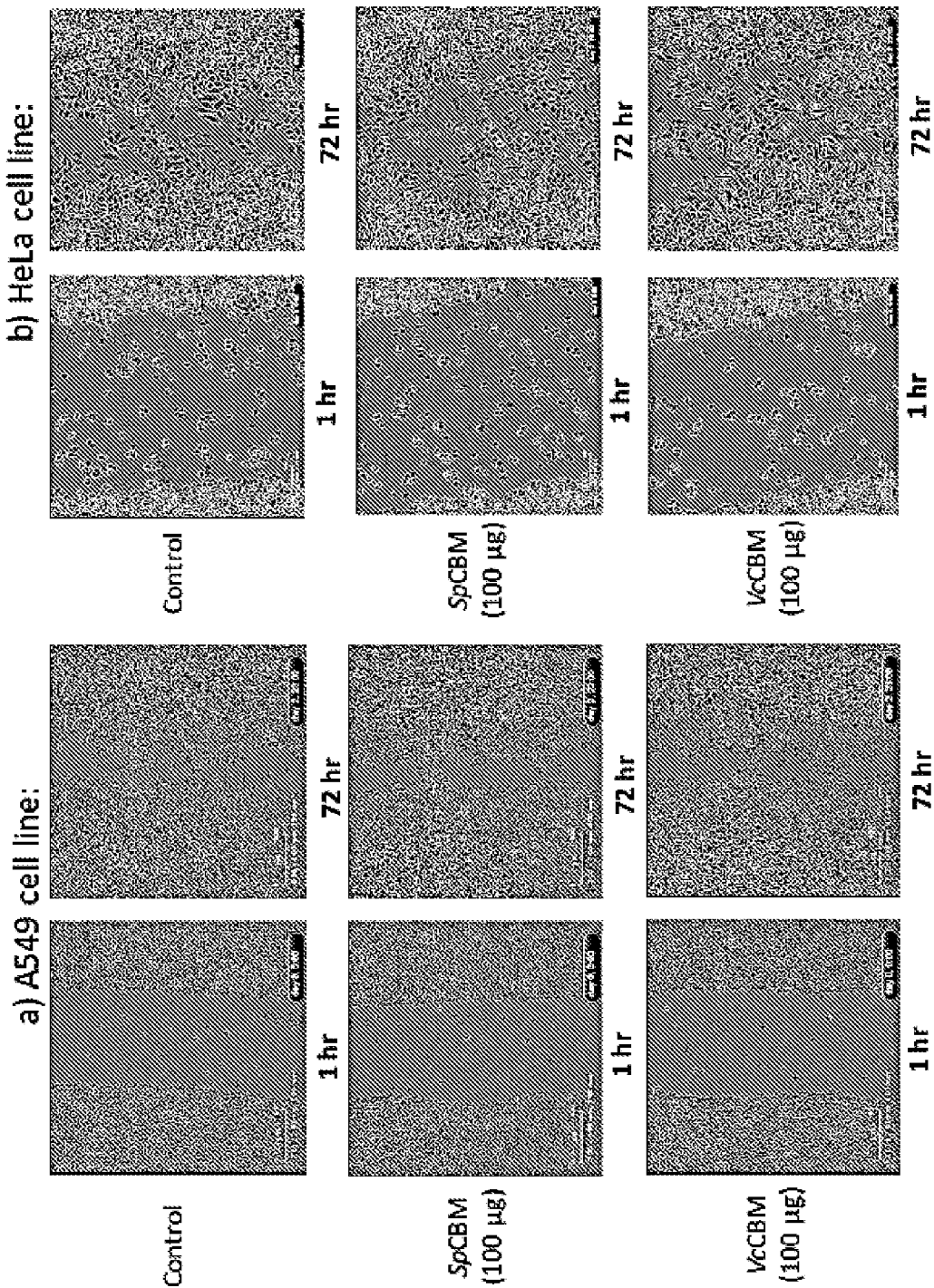
Figure 10B:
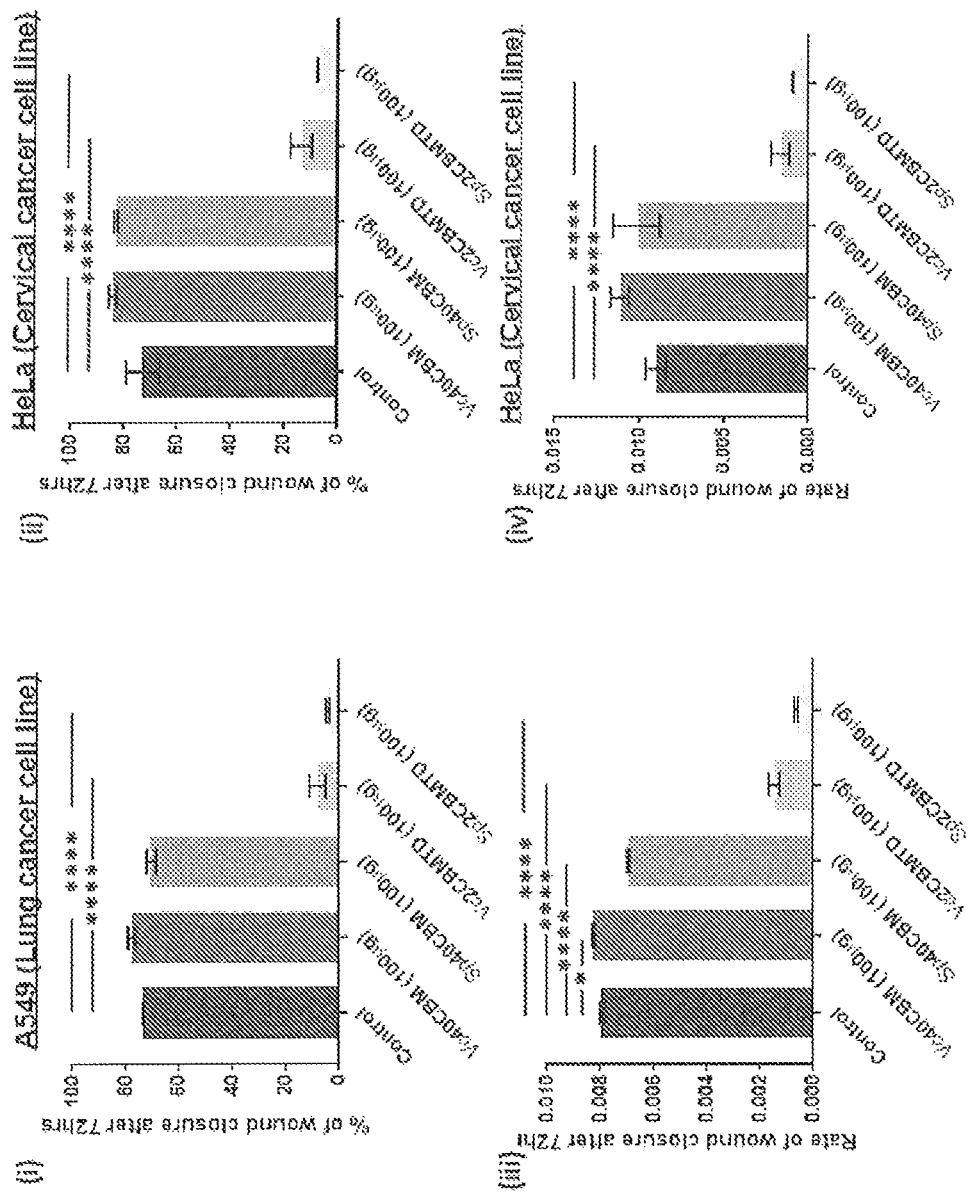

FIG. 10: Effect of component parts of engineered multimeric CBM40s on cell proliferation of cancer cell lines using a wound healing assay after 72 h. Monomeric (VcCBM, SpCBM) and multimeric (Vc2CBMTD and Sp2CBMTD) CBM40s were tested at 100 µg in a 250 µL volume representing a concentration of 400 µg/mL. A Images representing wound healing assay in A459 (a) and HeLa (b) cells after 1 h and 72 h, after treatment with PBS, SpCBM, or VcCBM in serum-free DMEM. Yellow bar at bottom of each image indicate diameter of 400 µm. B Graphs representing percentage (i) (ii), and rate (iii) (iv) of wound closure in the presence and absence of CBM after 72 h in A549 and HeLa cell lines, respectively. Dunnett's multiple comparison test was performed on the data and a statistical significance (p) of 0.0001 is highlighted by **** and a p of 0.05 is highlighted by *.

FIG. 11: Effect of component parts of engineered multimeric CBM40s on cell proliferation of A459 (A) and HeLa (B) cell lines using a wound healing assay after 72 h. The trimerization domain (TD) was tested at 100 µg in a 250 µL volume representing a concentration of 400 µg/mL. (a) Graph representing percentage of A549 cell wound closure in the presence and absence of TD after 72 hrs. Unpaired t test performed on data, no statistical significance (p) was reported between control and TD (p=0.1201). (b) Graph representing percentage of HeLa cell wound closure in the presence and absence of TD after 72 hrs. Unpaired t test performed on data, no statistical significance (p) was reported between control and TD (p=0.1201). (c). Graph representing the rate of A549 cell wound closure in the presence and absence of CBM after 72 hrs. Unpaired t test performed on data, a p of 0.05 was reported between control and TD (p=0.0212) highlighted by *. (d). Graph representing the rate of HeLa cell wound closure in the presence and absence of TD after 72 hrs. Unpaired t test performed on data, a p of 0.05 was reported between control and TD (p=0.0338) highlighted by *.

Figure 12:
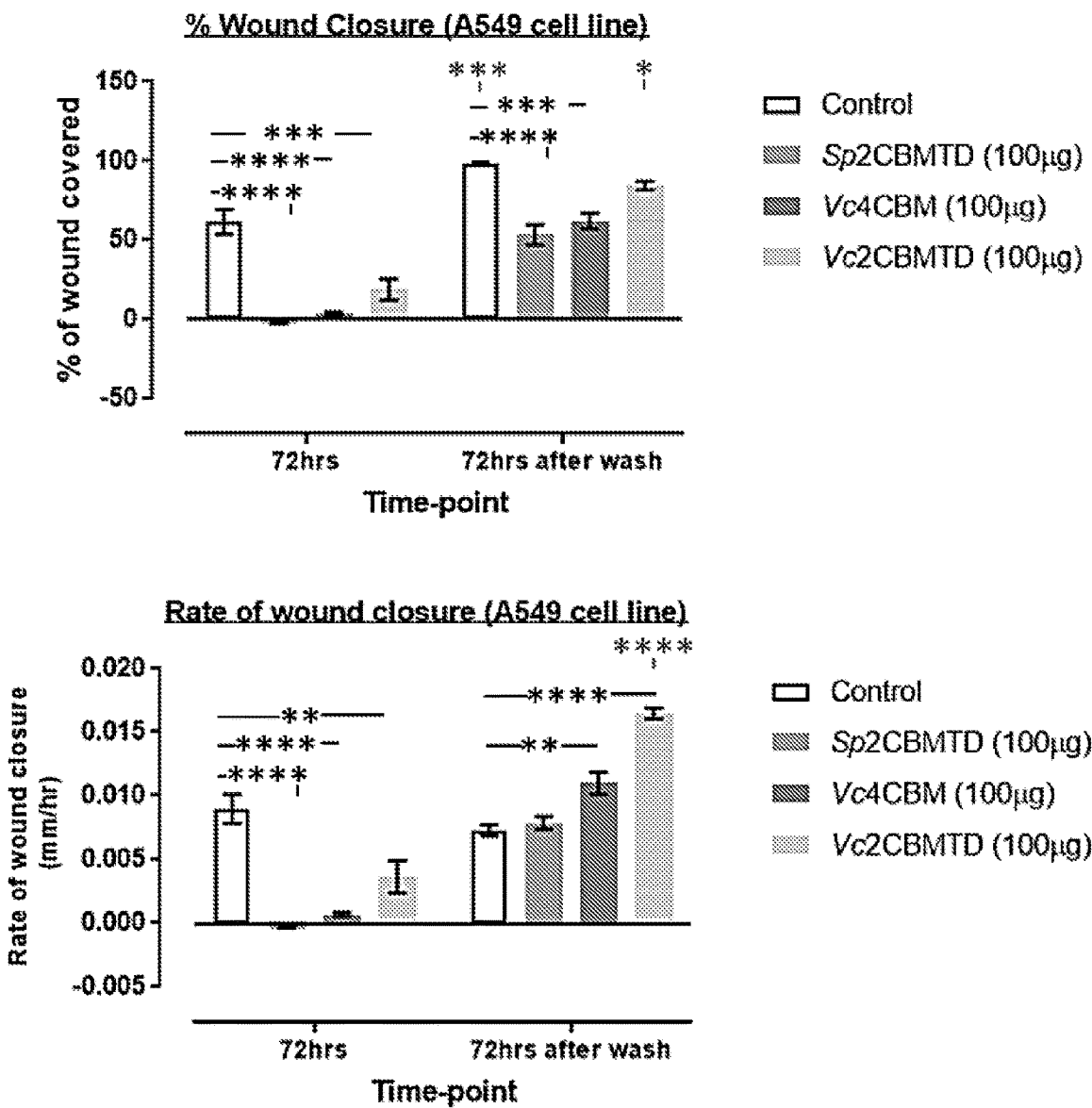

FIG. 12: Scratch assay data plus wash off for A549 cell line in the presence and absence of CBM after 72 hrs followed by a further 72 hrs after wash off. A one-way ANOVA and a Dunnett's multiple comparison test were performed on the data and a statistical significance (p) of 0.0001 is highlighted by **. A p of 0.0002 is highlighted by *. (a). The p of 0.0001, 0.0002 and 0.05 between the 72 hr control is represented by **, * and * respectively. (a). Graph representing percentage of A549 cell wound closure in the presence and absence of CBM after 72 hrs and 144 hrs after a CBM wash-off at the 72 hr time point (72 hrs after wash). (b). Graph representing the rate of A549 cell wound closure in the presence and absence of CBM after 72 hrs and 144 hrs after a CBM wash-off at the 72 hr time point (72 hrs after wash).

Figure 13:
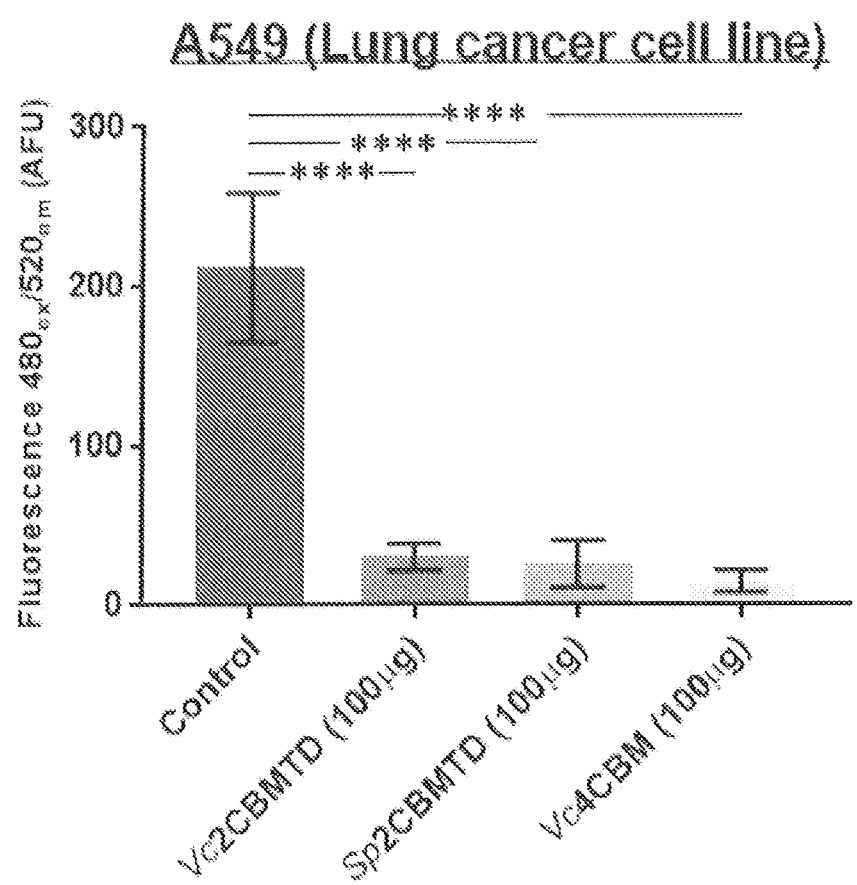

FIG. 13: Chemotaxis assay data from a lung cancer cell line (A549). A549 cells seeded at $8.0 \times 10^5$ cells/well. Fluorescence measured after 24 hrs background corrected. CBM tested at 100 µg in a 100 µL volume representing a concentration of 1 mg/ml. Dunnett's multiple comparison test was performed on the data and a statistical significance (p) of 0.0001 is highlighted by ****.

FIG. 14: Agglutination assay adapted from Hwang et al (1974). Graphs showing the absorbance at 546 nm of A549 cells in the absence (control) and presence of mCBM40 (Vc4CBM, Vc2CBMTD and Sp2CBMTD all at 1 mg/mL) for 5 mins, 30 mins and 1 hr (A), and at 1 hr and 24 hrs (B). A PBS only control was also included. Graphs showing the absorbance (C), and the rate of absorbance (D) of A549 cells at 546 nm for every ten seconds over 20 mins in the absence (control) and presence of mCBM40s after incubation on ice for 24 hrs.

Figure 15:
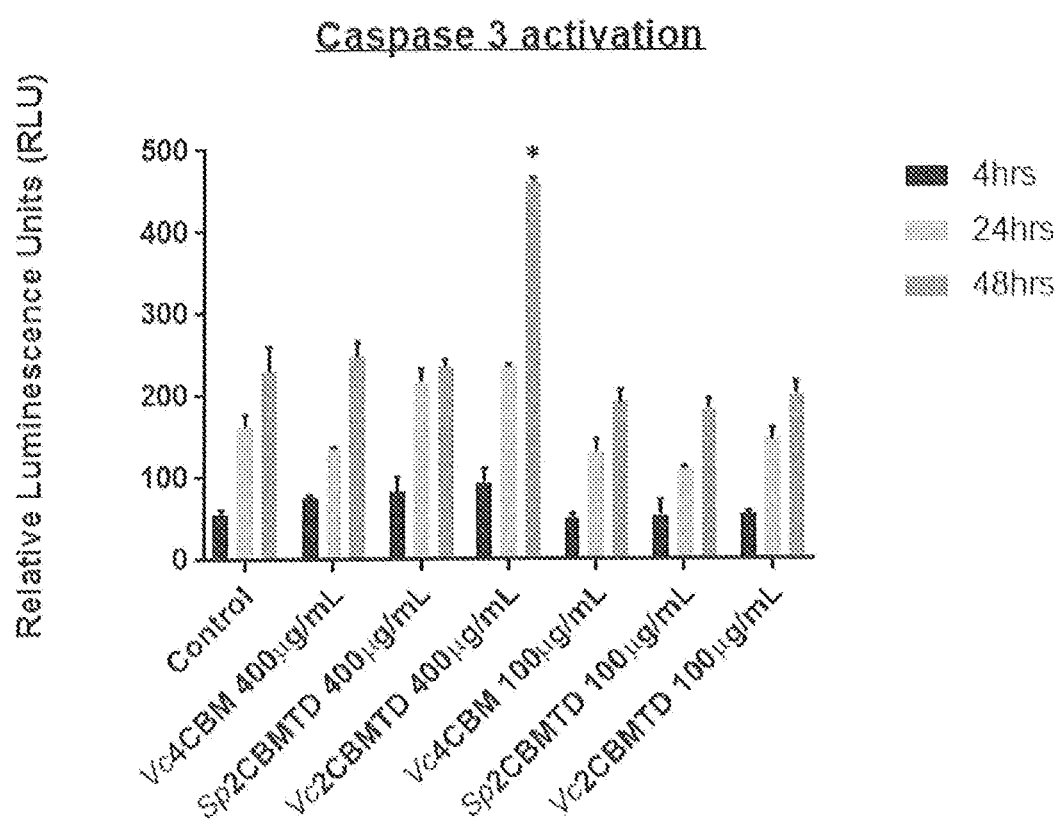

FIG. 15: Caspase dependent apoptosis. Graph showing the normalised (background corrected) luminescence signal produced by luciferase following caspase cleavage of Caspase-Glo® 3/7 reagent in A549 cells in the presence and absence of CBMs for 4 hrs, 24 hrs and 72 hrs. A one-way ANOVA and a Dunnett's multiple comparison test were performed on the data and a statistical significance (p) of ≤0.05 is highlighted by *.

Figure 16:
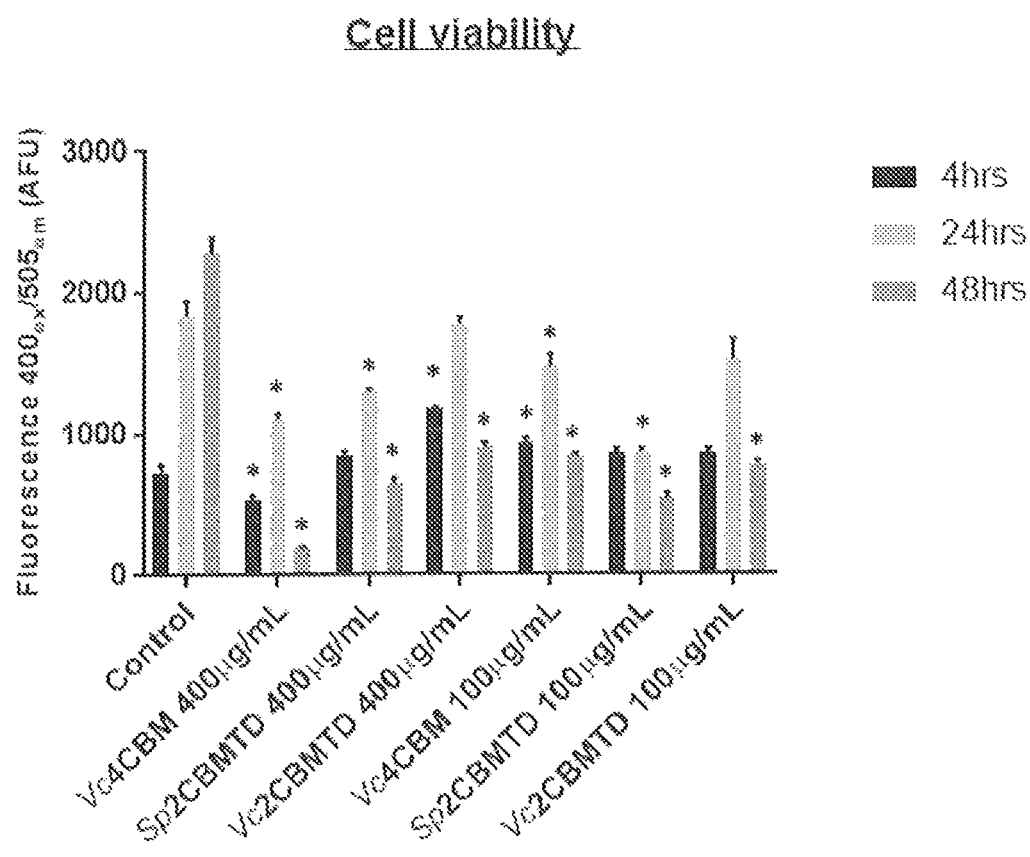

FIG. 16: Cell viability. Graph showing the normalised (background corrected) fluorescence signal produced by cleavage of GF-AFC substrate by A549 live cell protease in the presence and absence of CBMs for 4 hrs, 24 hrs and 72 hrs. A one-way ANOVA and a Dunnett's multiple comparison test were performed on the data and a statistical significance (p) of ≤0.05 is highlighted by *.

Figure 17:
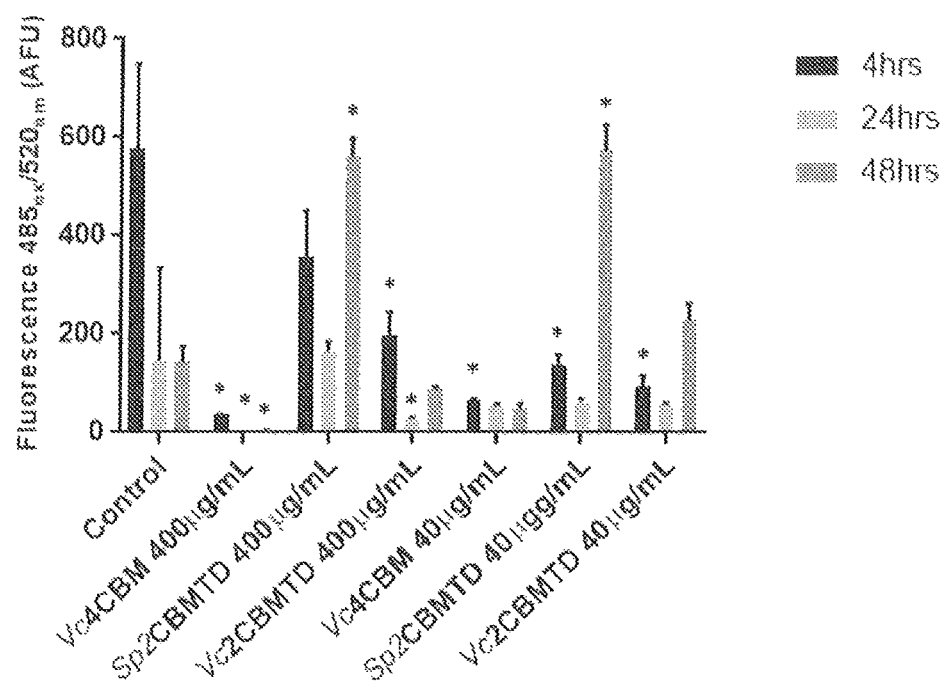

FIG. 17: Cell cytotoxicity data for lung cancer cell line A549 in the presence and absence of CBM. Graph showing the normalised (background corrected) fluorescence signal produced by cleavage of bis-AAF-R110 substrate by A549 dead cell protease in the presence and absence of CBMs for 4 hrs, 24 hrs and 72 hrs. A one-way ANOVA and a Dunnett's multiple comparison test were performed on the data and a statistical significance (p) of ≤0.05 is highlighted by *.

EXAMPLE 1

In an in vitro mCBM40 dosing experiment using confluent A549 human lung carcinoma cells and high concentrations of Sp2CBMTD (400-800 μg), little or no cell growth or activity was observed after 3 days. This was noted as the colour of the culture medium (DMEM/5% FCS), which would change colour as it is utilised, remained the same (see FIG. 2).

This observation led to the hypothesis that our engineered sialic acid-recognising CBMs might affect cell (including cancer cell) proliferation and migration by targeting sialylated host cell receptors.

To further support this hypothesis a wound scratch assay to determine cell migration and proliferation and a cell viability (MTT) assay were performed on A549 human lung carcinoma cells. These cells were treated with CBMs for 24 h. The results were compared to control cells that were given PBS only.

Figure 3:
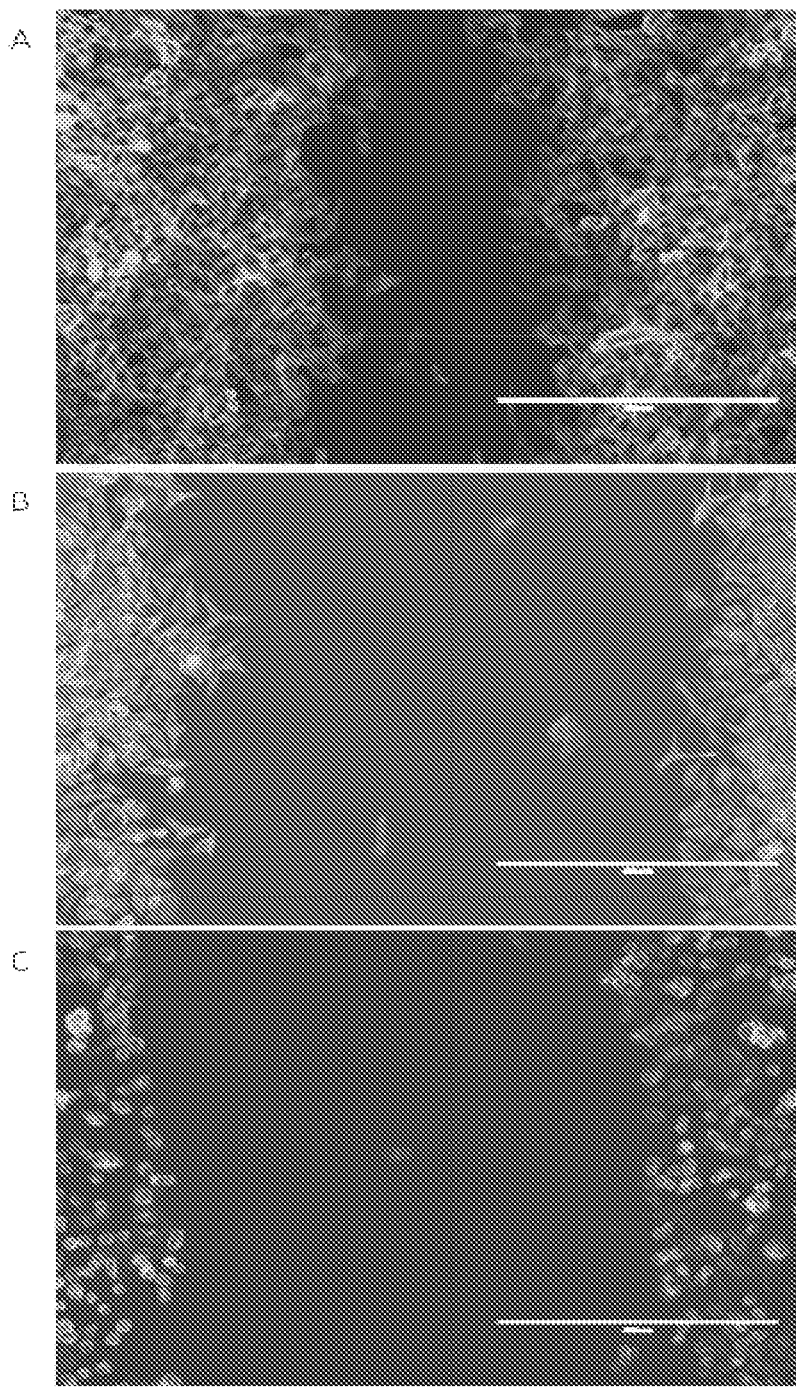
Figure 4:
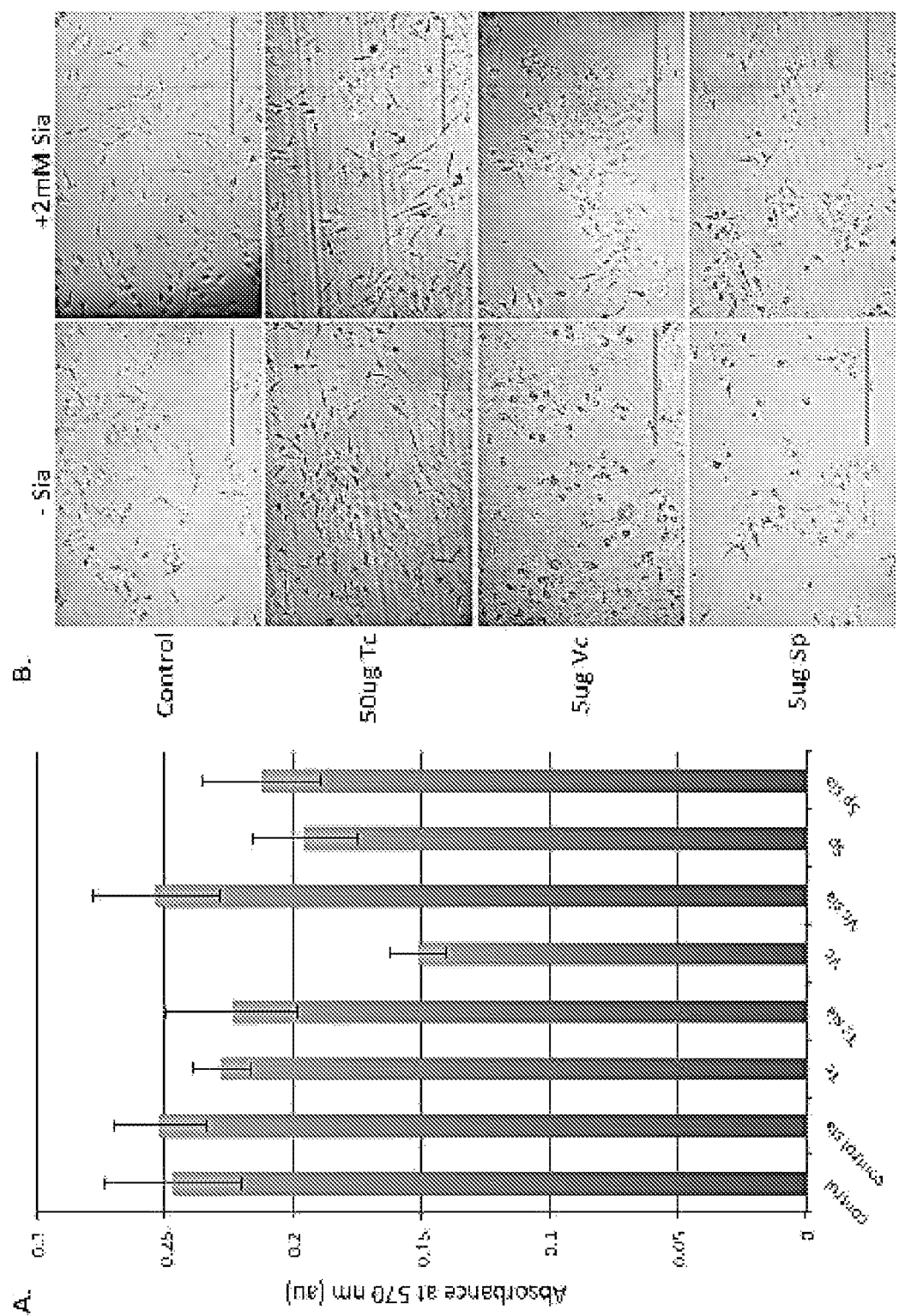

As seen in FIG. 3, little or no wound healing was observed in CBM-treated wells compared to PBS after 24 h. PBS-treated cells demonstrated a scratch diameter of 250 μm with lone cells migrating into the artificial wound after 24 h. In contrast, scratch diameters for both CBM-treated cells were roughly 710 μm, with changes in cell morphology likely associated with cell death or cell cycle arrest for the Vc2CBMTD-treated cells. There is also poor cell migration into the wound by Sp2CBMTD-treated A549 cells. Interestingly, the formation of filopodia was observed with Sp2CBMTD, a phenomenom usually coupled with cell motility (Mattila and Lappalainen, 2008).

Figure 2:

Metabolic activity decreased in cells that were given Vc2CBMTD in serum-free medium (absence of FCS), compared to cells that were given PBS only. Cell morphology of Vc2CBMTD-treated cells was also observed to have changed, with cells appearing more rounded (a sign of cell arrest) when compared to the control. Interestingly, cell metabolic activity and phenotype appeared to be reversed with the addition of 2 mM sialyllactose. Similar concentrations of sialic acid can also be found in FCS, and this may be the reason why Vc2CBMTD-treated cells remained viable after 3 days compared to Sp2-treated cells, which appear to be unaffected by the presence of FCS, at least at the high dose of CBM used in the assay (FIG. 2). Alternatively, it may be that free sialyllactose in the medium compete for the glycan binding sites of Vc2CBMTD, thus allowing A549 cells to recover and proliferate.

As for Sp2CBMTD-treated cells, there was also a slight (but not significant) decrease in metabolic activity. However, the lack of significance is likely due to the low concentration administered to the cells.

There was a slight recovery of cell growth in the presence of sialyllactose compared to Vc2-treated cells, but due to the nature of Sp2CBMTD, which is also known to stimulate pro-inflammatory mediators, it is likely that the phenomenon observed in FIG. 2, could be due to its immunomodulatory role. It has been demonstrated that Sp2CBMTD increased a number of inflammatory mediators such as IFN-γ, VEGF, IP-10 and IL-8 and other cytokines that are known to be important in neutrophil and macrophage targeting (Govorkova et al (2015). This feature may be ideal for targeting the immune system to cancer cells. As for TcTs-treated cells, the CBM-like domain had little effect on cell metabolism and morphology.

EXAMPLE 2

Wound Healing and Proliferation Assay of Cancer Cell Lines
Method:
All CBM40 proteins were prepared as described in Connaris et al (2014)[1]. The following cancer cell lines, A549 (human lung), HeLa (cervical), MDA.MB.231 and MCF-7 (breast), and SW620 and SW480 (colon) were purchased from ATCC. All cells with the exception of HeLa cells were maintained in 10% FBS, DMEM (high glucose with 1% Penicillin/Streptomycin) and incubated at 37° C. and 5% C02. HeLa cells expressing GFP restricted to the nucleus (using IncuCyte NucLight Green Lentivirus Reagent Cat No. 4626 Essen Biosciences) were maintained in complete medium containing 0.5 μg/ml Puromycin. For wound healing assays, 24 well plates (Nunc) were seeded with cells ($2.5 \times 10^5$ cells/well) and maintained in 500 μL of their respective maintenance medium and incubated at 37° C. and 5% $CO_2$ for 24 hrs. Wells were washed with 500 μL of serum-free DMEM, prior to the wound/scratch creation. A wound/scratch was created as a straight line down the middle of the well (running from the top to bottom of the well) in each well using a sterile 200 μL pipette tip (Axygen). Wells were then washed with 500 μL of serum-free DMEM prior to the addition of 250 μL of appropriately diluted CBMs, also prepared in serum-free DMEM. Serum-free medium was also included to wells as a control. Plates were incubated at 37° C. and 5% $CO_2$ for 10-30 mins before a further addition of 250 μL of 4% FBS, DMEM to each well (2% FBS final concentration) so that the final CBM concentration ranged from 20-200 μg/ml. The IncuCyte ZOOM (Essen BioScience) apparatus was used to collect time-lapse images of each well. This was set to collect three images of the wound/scratch in each well every 1 hr for 72 h. For data collection, the IncuCyte ZOOM 2016 software was used to measure and collate wound width measurements for each image (3× wound measurements were performed manually). For the cell proliferation assay, GFP-labelled HeLa cells were grown in 24 well plates over 72 h in the presence or absence of mCBM40s. Cell proliferation is monitored by analysing the occupied area (percentage of confluence) of cell images over time using the IncuCyte ZOOM apparatus. Cell proliferation is directly proportional to increase in confluence.

Figure 5:
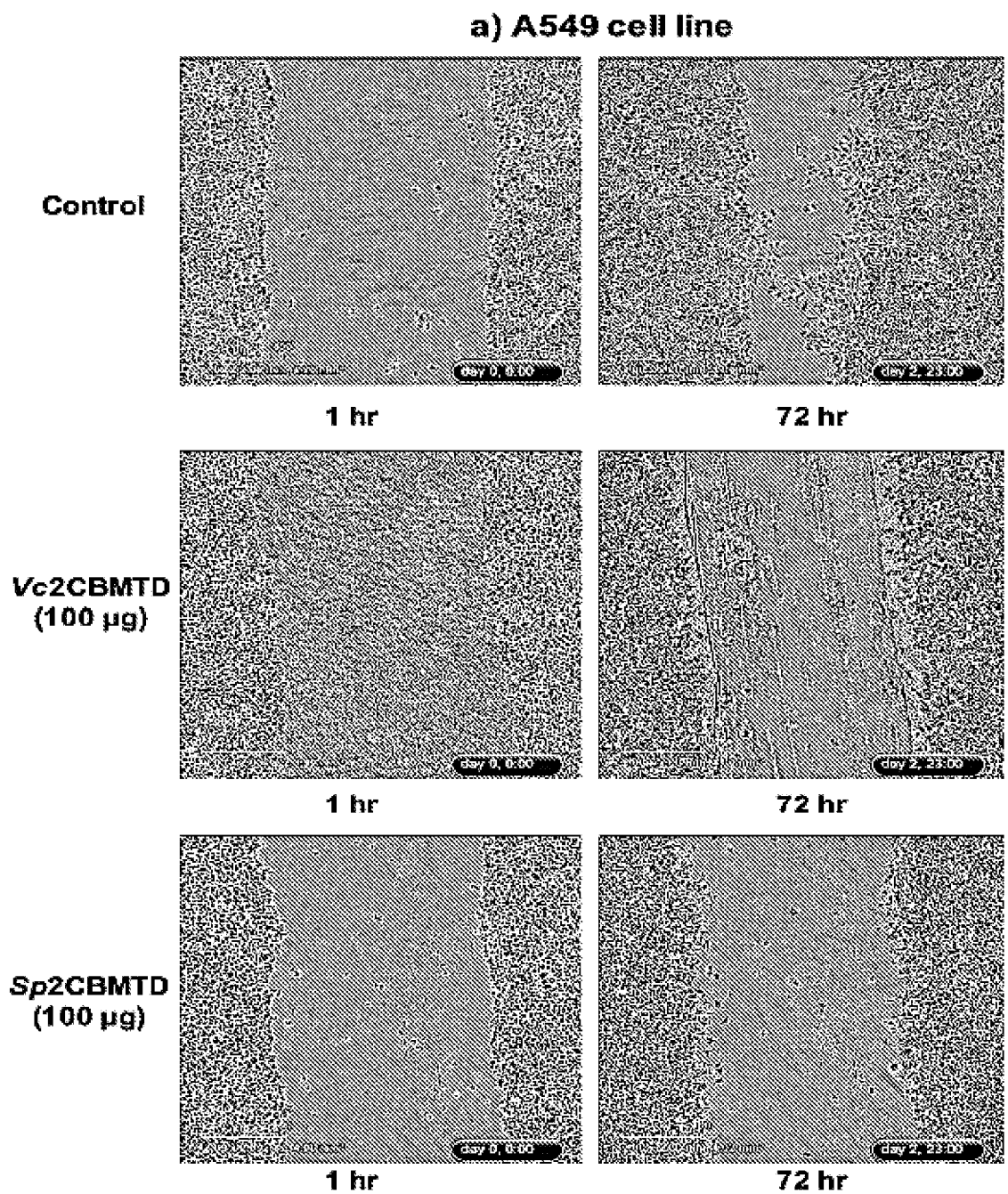
Figure 5B:
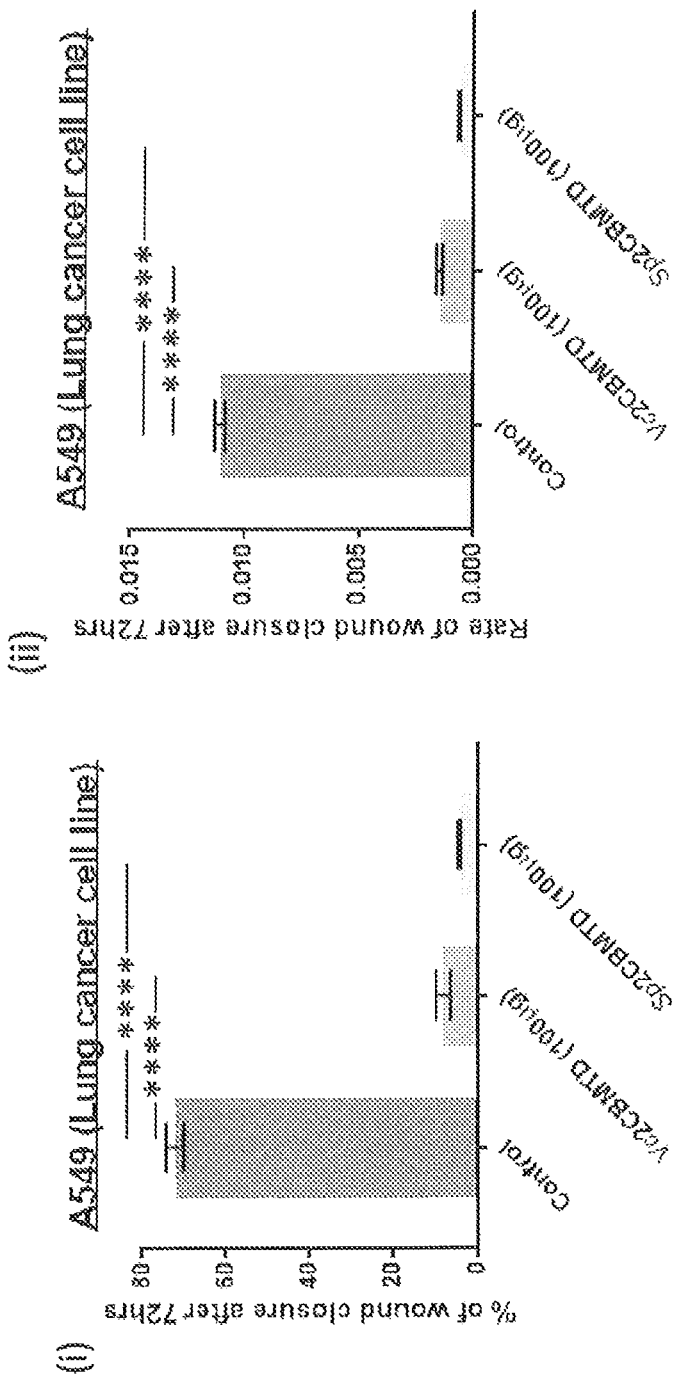
Figure 6A:
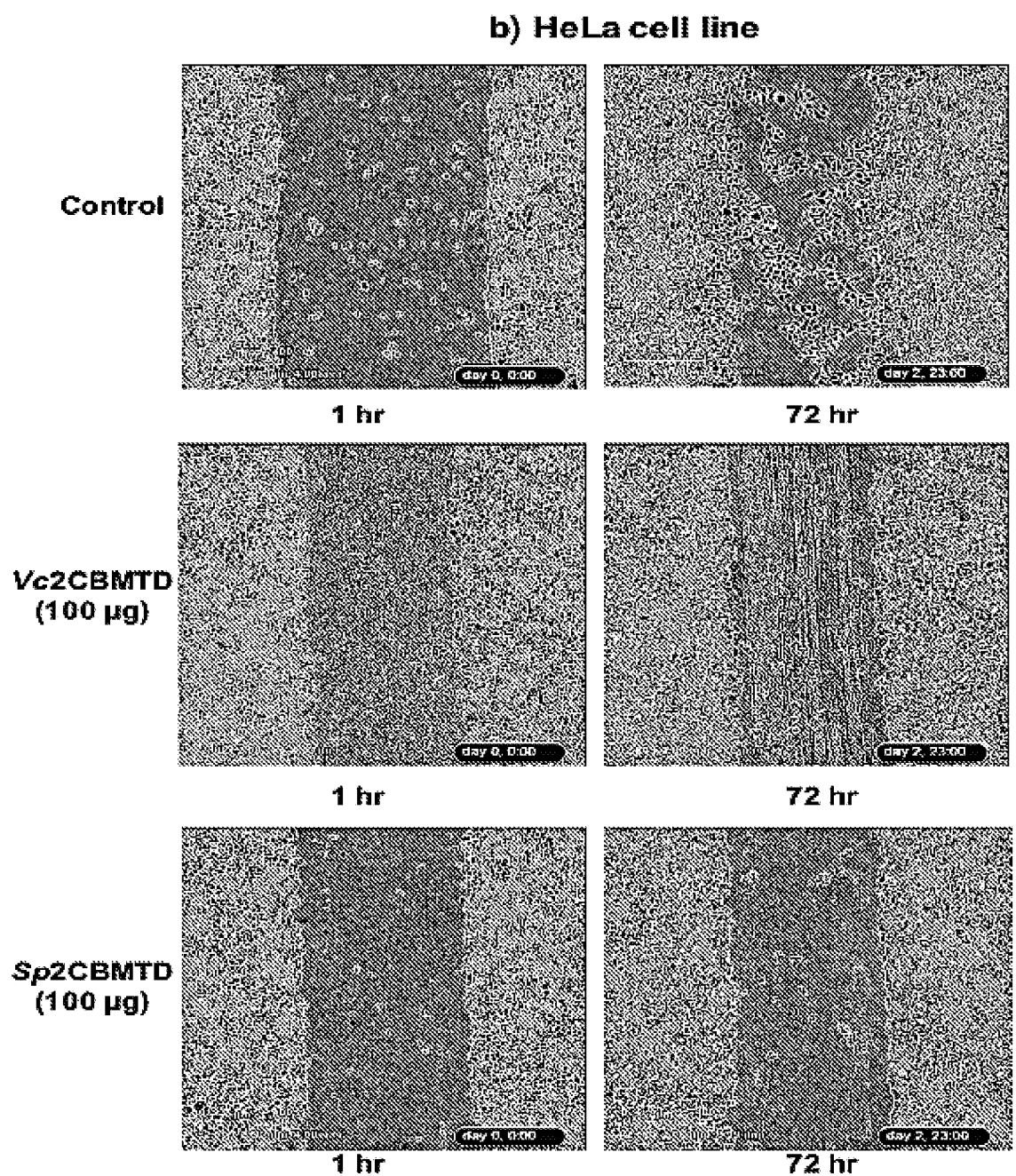
Figure 6B:
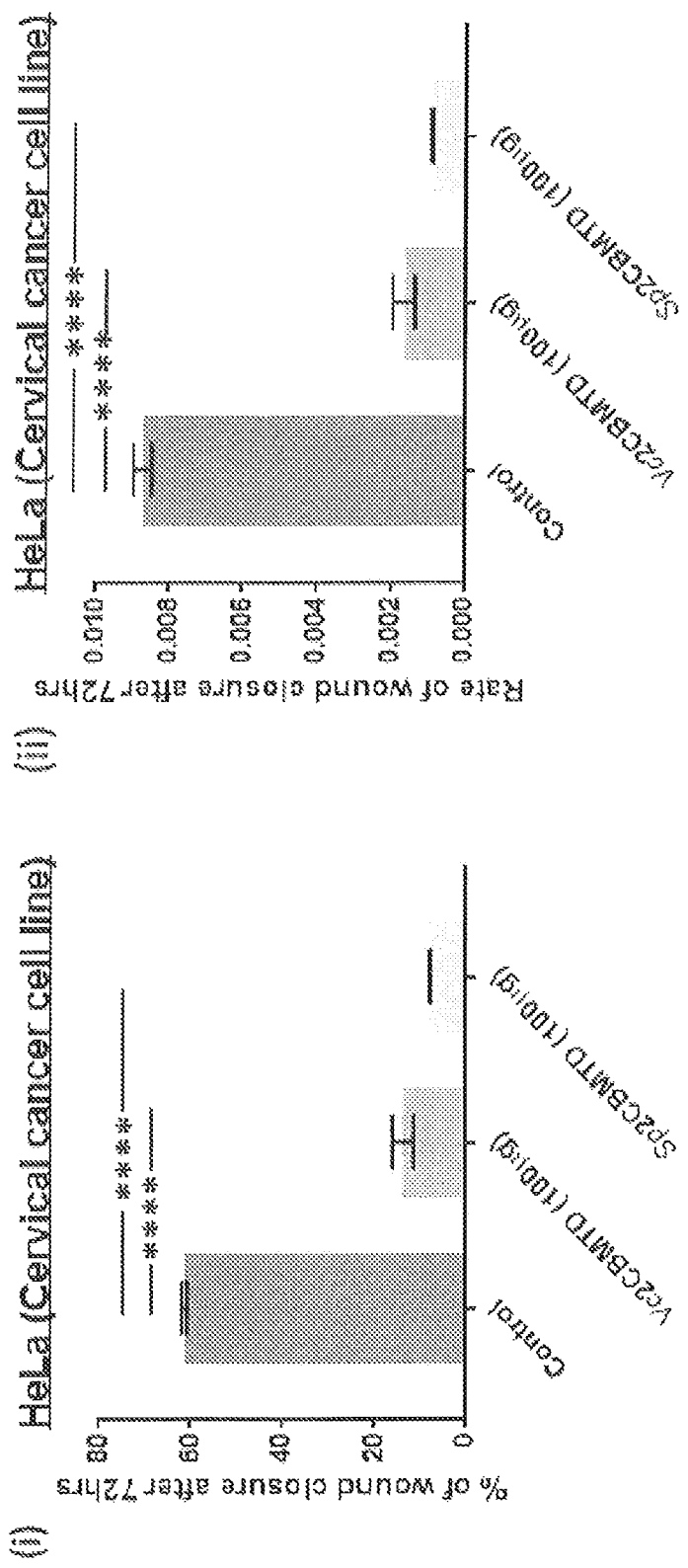

Results:
FIGS. 5 and 6 illustrate the results of a wound-healing assay measuring the effect of different hexameric mCBM40s against different cancer cell types A549 and HeLa. The results indicate that hexameric CBM40s Vc2CBMTD and Sp2CBMTD significantly inhibited wound closure in both cancer types after 72 h compared to cells that were left untreated. Multimeric CBMs also inhibited wound closure in other cancer types that displayed differential expression of sialylated receptors. The cell growth of both breast and colon cancers were found to be inhibited in a dose-dependent manner (FIG. 7 illustrates the results from the highest dose of mCBM40s used against two metastatic cell types of breast and colon cancer). A difference in potency was observed between the highly metastatic and lowly metastatic breast cancer cell lines MDA.MB.231 and MCF-7. Multimeric CBMs were more potent against the MDA.MB.231 cell line. The potency did not differ much between the colon cancer cell lines SW620 and SW480 despite different glycosylation profiles. The percentage of wound covered for the two colon cancer cell lines and the low-grade breast cancer cell line after 72 hrs was low (between 30% to 40%).

The inhibition of wound healing was due to the lack of cell proliferation over time as shown in FIG. 8, using GFP-labelled HeLa cells that demonstrated reduced cell growth over time. The anti-proliferative effect of mCBM40s was also observed with a tetrameric version mCBM40, Vc4CBM in both A549 and HeLa cells (FIG. 9).

To determine whether the anti-proliferative effect is a result of the multimeric nature of engineered CBMs, A549 and HeLa cell lines were treated with the monomeric versions of Vc- and Sp-based CBM40s (VcCBM, SpCBM, 100 µg each) and left to incubate for up to 72 h. The data was then compared with that of their multimeric counterparts. FIG. 10 illustrates the results of a wound healing assay of A549 and HeLa cell lines after treatment with CBMs. At the dose used, multimeric CBMs had a significant effect on the rate of wound closure.

Furthermore, the non-CBM40 component of mCBM40s, that is, the trimerisation domain (TD), was also tested in a scratch assay to determine if this domain may contribute to the anti-proliferative effect seen in the scratch assays. FIG. 11 demonstrates that the TD domain, when given at the same dose as the CBMs, does not appear to affect the cell growth or proliferation of A549 or HeLa cells, as the percentage and rate of wound closure was identical to untreated cells.

To establish if anti-proliferative activity of CBM proteins can be reversed after a wound scratch assay, a wash-off experiment was attempted. After 72 h incubation, treated wells were washed twice with 0.5 mL of 2% FBS, DMEM (high glucose, 1% Penicillin/Streptomycin). The same medium (0.5 mL) was then added to each well and incubated for a further 72 h. The EVOS FL (ThermoFisher Scientific) apparatus was used to manually collect three images of the wound/scratch in each well at 0 hrs and 72 hrs. Image J software was used to manually measure and collate wound width measurements for each image (Image J measurement tool was calibrated against a scale bar for the EVOS FL). After removal of mCBM40s, cells were clearly seen to migrate and/or proliferate into the wound (FIG. 12). The rate and percentage of wound closure was observed to revert to "normal"/control back after the wash off. The rate of wound closure for VcCBM2TD after wash off was observed to be slightly faster than that of the control condition after 72 hrs. These observations suggest that mCBM40s can modulate the cell response to cancer by interacting with sialylated cell surface receptors.

Migration Assay.
Method:
A Boyden chamber assay was selected to determine if cellular migration is interrupted by multimeric CBM40s. The Boyden chamber assay (8 µm, fluorometric format) was prepared as described in manufacturer's instructions (Cell Biolabs CytoSelect 96-well cell migration assay). Final CBM concentration ranged from 20-200 µg/ml.
Results:
FIG. 13 illustrate the results from the migration assay, which indicate that the CBMs tested inhibited migration of A549 cells. To eliminate the possibility that the lack of migration may be attributed to agglutination of A549 cells by mCBM40s when added directly to cell suspension, an agglutination assay was also performed using a spectrophotometric assay (Hwang et al, 1974)$^2$. The rate of absorbance/sedimentation of A549 cells over time did not differ greatly between the conditions (FIG. 14, A). This was further validated with a longer duration agglutination assay and a rate of absorbance/kinetics assay (FIGS. 14, B, C and D). This suggests that no agglutination of A549 cells (at $0.8 \times 10^6$ cells/mL) in the presence of 1 mg/mL mCBM40 occurs. The inhibition of A549 cell chemotaxis can, therefore, be attributed to the direct inhibition of cellular migration and not cellular agglutination.

Cell Apoptosis, Viability and Cytotoxicity Assay.
Method:
To determine if multimeric CBMs cause cell apoptosis, the Promega ApoTox-Glo™ Triplex Assay was used. This assay was performed using A549 cells. 10,000 cells per well were seeded 24 hrs prior to experiment. CBMs and controls were added to wells to a final volume of 100 µL with final CBM concentrations of 0.1-1 mg/ml. Cells were cultured in conditions for test exposures of 4 hrs, 24 hrs, 48 hrs and 72 hrs (FIG. 8).
Results:
After 48 hrs, Vc2CBMTD (at 400 µg) showed elevated luminescence signal corresponding to activation of caspase 3 (a hallmark of apoptosis). All the other conditions at 4 hrs, 24 hrs and 48 hrs showed similar luminescence levels to that of the untreated cells (FIG. 11). The fluorescence signal for the cleaved AFC is lower in CBM conditions after 48 hrs (FIG. 12). This might be due to either reduced permeability of the substrate, cells entering into a dormant state and/or cell cycle arrest. During most cytotoxic events, viability and cytotoxic measures will be inversely proportional; a reduction in viability without an increase in cytotoxicity is seen for compounds/drugs that alter normal cell division (i.e. cell cycle arrest) without producing membrane integrity changes. A number of the CBMs showed a decreased level of fluorescence for R110 indicating low levels of cytotoxicity (FIG. 13). Results from this cell viability, cytotoxicity and apoptosis experiment suggest that in the presence of mCBM40s, A549 cells are in cell cycle arrest or a state of dormancy.

Discussion

The results identify that CBMs (Vc4CBM, Vc2CBMTD and Sp2CBMTD), but not the non-CBM component (TD), inhibit cellular behaviours required for wound healing (proliferation and migration) and are effective against multiple cancer types as indicated by experiments using breast, colon, cervical and lung cells. Agglutination of the A549 cell line was not observed. The inhibition of both migrating and proliferating cells in the wound-healing assay can be reversed via a wash-off. The results obtained from the Promega ApoTox-Glo™ Triplex Assay suggest that CBMs cause cell cycle arrest/or dormancy in the A549 cell line.

References for Example 1

Astarita, J L. et al., (2012). Frontiers in Immunology 3:283.
Connaris, H et al., (2009). Journal of Biological Chemistry 284: 7339-7351.
Connaris, H. et al., (2014). PNAS 111:6401-6406.
Govorkova, E A et al., (2015). Antimicrobial Agents and Chemotherapy 59:1495-1504.
Kato, Y. et al., (2005) Tumour Biology 26: 195-200.
Mattila, P K. and Lappalainen, P. (2008). Nature Reviews Molecular Cell Biology 9: 446-454.
Müthing, J. et al., (2002). Glycobiology 12: 485-497.
Ochoa-Alvarez, J A. et al., (2012). PLoSONE 7:e41845.
Schacht, V. et al., (2005). American Journal of Pathology 166: 913-921.
Shibahara, J. et al., (2006). Virchow Arch. 448:493-499.
Yau, T. et al., (2015) Molecules 20: 3791-3810.

Zwierzina, H. et al., (2011) European Journal of Cancer 47: 1450-1457.

References for Example 2

[1]. Connaris H, Govorkova E A, Ligertwood Y, Dutia B M, Yang L, Tauber S, Taylor M A, Alias N, Hagan R, Nash A A, Webster R G, Taylor G L. 2014. Prevention of influenza by targeting host receptors using engineered proteins. Proc Natl Acad Sci USA 111:6401-6406.

[2]. Hwang, K. M., Murphree, S. A. and Sartorelli, A. C., 1974. A quantitative spectrophotometric method to measure plant lectin-induced cell agglutination. Cancer Research, 34(12), pp. 3396-3402.

The invention claimed is:

1. A method of treating cancer, said method comprising administering a sialic acid binding molecule to a subject in need thereof, wherein the sialic acid binding molecule is a multimeric carbohydrate binding module (CBM).

2. The method of claim 1, wherein the cancer is lung cancer, cervical cancer, colon cancer and/or breast cancer.

3. The method of claim 1, wherein the multimeric carbohydrate binding module comprises one or more family 40 carbohydrate binding module(s).

4. The method of claim 1, wherein the multimeric carbohydrate binding module comprises a sialic acid binding domain of *Vibrio cholerae* NanH sialidase and/or a sialic acid binding domain of *Streptococcus pneumoniae* NanA sialidase.

5. The method of claim 4, wherein the *Vibrio cholerae* NanH sialidase comprises the amino acid sequence of SEQ ID NO: 1 or 2.

6. The method of claim 4, wherein the *Streptococcus pneumoniae* NanA sialidase comprises the amino acid sequence of SEQ ID NO: 3 or 4.

7. The method of claim 1, wherein the multimeric CBM comprises two or more sialic acid binding domains of *Vibrio cholerae* NanH sialidases and/or two or more sialic acid binding domains of *Streptococcus pneumoniae* NanA sialidases.

8. The method of claim 1, wherein the multimeric CBM comprises 2, 3, 4, 5, 6, 7, 8, 9 or 10 sialic acid binding domains of *Vibrio cholerae* NanH sialidases and/or *Streptococcus pneumoniae* NanA sialidases.

9. The method of claim 1, wherein the multimeric CBM is a combination of four sialic acid binding domains of *Vibrio cholerae* NanH sialidase (Vc4CBM), a combination of two sialic acid binding domains of *Vibrio cholerae* NanH sialidase and a trimerisation domain (Vc2CBMTD), and/or a combination of two sialic acid binding domains of *Streptococcus pneumoniae* NanA sialidase and a trimerisation domain (Sp2CBMTD).

* * * * *

UNITED STATES PATENT AND TRADEMARK OFFICE
CERTIFICATE OF CORRECTION

| | |
|---|---|
| PATENT NO. | : 11,389,502 B2 |
| APPLICATION NO. | : 16/332926 |
| DATED | : July 19, 2022 |
| INVENTOR(S) | : Connaris et al. |

It is certified that error appears in the above-identified patent and that said Letters Patent is hereby corrected as shown below:

On the Title Page

(30) Foreign Application Priority Data: Please correct "1616006" to read --1616006.1--

In the Specification

Column 5, Line 10: Please insert a paragraph break between "moieties"" and "The sialic"

Signed and Sealed this
Twenty-second Day of November, 2022

Katherine Kelly Vidal
*Director of the United States Patent and Trademark Office*